United States Patent

Nishimura

[11] Patent Number: 5,552,854
[45] Date of Patent: Sep. 3, 1996

[54] VISUAL LINE DETECTION DEVICE AND CAMERA EQUIPPED THEREWITH

[75] Inventor: Hitoshi Nishimura, Komae, Japan

[73] Assignee: Nikon Corporation, Tokyo, Japan

[21] Appl. No.: 341,988

[22] Filed: Nov. 16, 1994

Related U.S. Application Data

[63] Continuation of Ser. No. 118,607, Sep. 10, 1993, abandoned.

[30] Foreign Application Priority Data

Sep. 14, 1992 [JP] Japan ................................ 4-245143

[51] Int. Cl.⁶ ........................... G03B 13/02; A61B 3/113
[52] U.S. Cl. ........................ 354/410; 354/219; 351/210
[58] Field of Search ...................... 354/410, 432, 354/478, 219, 62; 351/210, 211; 250/221

[56] References Cited

U.S. PATENT DOCUMENTS

| | | | |
|---|---|---|---|
| 5,036,347 | 7/1991 | Tsunekawa et al. | 354/400 |
| 5,182,443 | 1/1993 | Suda et al. | 354/219 X |
| 5,225,862 | 7/1993 | Nagano et al. | 354/62 |
| 5,231,674 | 7/1993 | Cleveland et al. | 351/210 |
| 5,280,312 | 1/1994 | Yamada et al. | 351/211 |

FOREIGN PATENT DOCUMENTS

| | | |
|---|---|---|
| 3841575 | 7/1989 | Germany . |
| 2-264632 | 10/1990 | Japan . |
| 3-109029 | 5/1991 | Japan . |
| 4-347127 | 2/1992 | Japan . |
| 4-240438 | 8/1992 | Japan . |
| 6-138371 | 5/1994 | Japan . |
| 6-261863 | 9/1994 | Japan . |
| 6-319701 | 11/1994 | Japan . |

*Primary Examiner*—W. B. Perkey
*Attorney, Agent, or Firm*—Oliff & Berridge

[57] ABSTRACT

The visual line detection device according to the present invention is capable of accurately detecting the visual line of the eyeball of an observer, even though it uses light sources which are only a finite distance away from the eyeball, i.e. which are not effectively at infinity. At least two infrared light emitting diodes are provided for illuminating the eyeball, and the position of the center of curvature of the cornea of the eyeball is obtained based upon the positions of a plurality of images generated by the light rays emitted by these diodes being reflected from the cornea. The direction of the visual line of the eyeball is then calculated using this position of the center of curvature of the cornea. A camera according to the present invention is also disclosed which incorporates such a visual line detection device.

17 Claims, 29 Drawing Sheets

FIG. 8A

S101 READ IN FROM THE PHOTOELECTRIC CONVERSION DEVICE 17 POSITION COORDINATES $(x'_{dL}, z'_{dL})$ AND $(x'_{dR}, z'_{dR})$ FOR THE BOUNDARY BETWEEN THE PUPIL AND THE IRIS

S102 CONVERT THE POSITION COORDINATES $(x'_{dL}, z'_{dL})$ AND $(x'_{dR}, z'_{dR})$ FOR THE BOUNDARY BETWEEN THE PUPIL AND THE IRIS TO ACTUAL SPACE COORDINATES USING $x_{dL}=f_x(x'_{dL}, z'_{dL})$, $z_{dL}=f_z(x'_{dL}, z'_{dL})$, $x_{dR}=f_x(x'_{dR}, z'_{dR})$, AND $z_{dR}=f_z(x'_{dR}, z'_{dR})$

S103 CALCULATE THE COORDINATES $(X_d, Z_d)$ OF THE CENTER OF THE PUPIL USING $X_d=(x_{dL}+x_{dR})/2$, $Z_d=(z_{dL}+z_{dR})/2$

S104 READ IN FROM THE PHOTOELECTRIC CONVERSION DEVICE THE POSITION COORDINATES $(X1'_{p1}, Z1'_{p1})$ OF THE FIRST PURKINJE IMAGE CREATED BY IRED1

START

S201 — READ IN FROM THE PHOTOELECTRIC CONVERSION DEVICE THE POSITION COORDINATES $(x'dL, z'dL)$ AND $(x'dR, z'dR)$ FOR THE BOUNDARY BETWEEN THE PUPIL AND THE IRIS

S202 — CONVERT THE POSITION COORDINATES $(x'dL, z'dL)$ AND $(x'dR, z'dR)$ FOR THE BOUNDARY BETWEEN THE PUPIL AND THE IRIS TO ACTUAL SPACE COORDINATES USING $xdL=fx(x'dL, z'dL)$, $zdL=fz(x'dL, z'dL)$, $xdR=fx(x'dR, z'dR)$, AND $zdR=fz(x'dR, z'dR)$

S203 — CALCULATE THE COORDINATES $Xd$, $Zd$ OF THE CENTER OF THE PUPIL USING $Xd=(xdL+xdR)/2$, $Zd=(zdL+zdR)/2$

S204 — READ IN FROM THE PHOTOELECTRIC CONVERSION DEVICE THE POSITION COORDINATES $(X1'p1, Z1'p1)$ OF THE FIRST PURKINJE IMAGE CREATED BY IRED1

S205: CONVERT THE POSITION COORDINATES (X1'p1, Z1'p1) OF THE FIRST PURKINJE IMAGE TO ACTUAL SPACE COORDINATES USING X1p1=fx(X1'p1, Z1'p1) AND Z1p1=fz(X1'p1, Z1'p1)

S206: READ IN FROM THE PHOTOELECTRIC CONVERSION DEVICE THE POSITION COORDINATES (X2'p1, Z2'p1) OF THE FIRST PURKINJE IMAGE CREATED BY IRED2

S207: CONVERT THE POSITION COORDINATES (X2'p1, Z2'p1) OF THE FIRST PURKINJE IMAGE TO ACTUAL SPACE COORDINATES USING X2p1=fx(X2'p1, Z2'p1) AND Z2p1=fz(X2'p1, Z2'p1)

S208: IS $(Sx1-X1p1) \times (Sz2-Z2p1) - (Sx2-X2p1) \times (Sz1-Z1p1)$ LESS THAN OR EQUAL TO $\varepsilon$ ?

FIG. 16

S209: READ IN FROM THE PHOTOELECTRIC CONVERSION DEVICE THE POSITION COORDINATES (X3'p1, Z3'p1) OF THE FIRST PURKINJE IMAGE CREATED BY IRED3

S210: CONVERT THE POSITION COORDINATES (X3'p1, Z3'p1) OF THE FIRST PURKINJE IMAGE TO ACTUAL SPACE COORDINATES USING X3p1=fx(X3'p1, Z3'p1) AND Z3p1=fz(X3'p1, Z3'p1)

S211: SUBSTITUTE X3p1 AND Z3p1 FOR X1p1 AND Z1p1

S212: OBTAIN THE DIRECTION θ, L, Φ, AND k OF THE VISUAL LINE BY SUBSTITUTING X1p1, Z1p1, X2p1, Z2p1, Xd, AND Zd INTO THE EQUATIONS (17) THROUGH (20)

END (A)

(B)

(C)

VISUAL LINE DETECTION DEVICE AND CAMERA EQUIPPED THEREWITH

This is a continuation of application Ser. No. 08/118,607 filed Sep. 10, 1993, now abandoned.

BACKGROUND OF THE INVENTION

1. Field of the Invention

The present invention relates to a visual line detection device which detects the direction of the point of attention towards which an observer is directing his attention within a field of view provided for example within an optical device, i.e., which detects the direction of the so called visual line, and also relates to a camera equipped with such a visual line detection device.

2. Description of Related Art

In art relating to devices for detecting the visual line of an observer, for example, there is a type of visual line detection device disclosed in Japanese Patent Laid Open Publication Heisei 3-109029, which it is not hereby intended to admit as prior art to the present application except to the extent in any case mandated by applicable law. With the device disclosed in this publication, the eyeball of the observer is illuminated by a light source. The central position of the pupil is determined by sensing the boundary between the pupil and the iris of the eyeball illuminated by this light source; The position of the image of the light source generated by the light rays from the light source and reflected from the cornea is determined. The visual line is determined from the relative positional relation of this pupil central position and the image reflected from the cornea. In the following, the operation of the visual line detection device according to the above identified publication will be explained with reference to FIG. 30.

FIG. 30 is a sectional view taken through a human eyeball in a horizontal plane. In this figure, the reference numeral 1 denotes the eyeball, and this eyeball 1 generally consists of a sclera 2 of generally spherical shape filled with a vitreous body 3, with a lens 4, an iris 5, and a cornea 6 being formed in the front portion of this sclera 2 (the upper left portion in the figure). The iris 5 is a membrane surrounding a central open portion or aperture 7 which is called the pupil, and said iris 5 includes muscles which can be contracted or relaxed so as to open or close said pupil 7. The curvature of the cornea 6 is substantially greater than the curvature of the sclera 2 and of the vitreous body 3 contained therein. If, as shown in the figure, the distance between the center of curvature C of the cornea and the center of rotation O' of the eyeball 1 is called ρ, and the distance between the center D of the pupil and the center of rotation O' of the eyeball is called A, then, although these distances do in fact vary slightly between individuals, they can be assumed to be almost constant in practice.

As shown in FIG. 30, the X axis is taken in a horizontal direction (the up and down direction in the figure), and the position along the X axis of the center of rotation O' of the eyeball when the eyeball 1 is applied squarely against the center of a plane of view not shown in the figure (and is thus in a different position, both angularly and in parallel displacement along the X axis, from its shown position) will be taken as the origin O. The position on the X axis of the center D of the pupil (this is also designated by the symbol D) and the position on the X axis of the image P reflected from the cornea (this is also designated by the symbol P) are given by, if the angle θ of rotation of the eyeball 1 is defined as shown in the figure:

$$D = L + A \times \sin\theta \quad (1)$$

$$P = L + \rho \times \sin\theta \quad (2)$$

Here, the image P reflected from the cornea is what is called the first Purkinje image, and is a virtual image created by light rays reflected from the surface of the cornea, when the cornea 6 is considered as a convex lens.

By substituting from equation (1) into equation (2), it is possible to eliminate the component L of parallel displacement of the center of rotation O' of the eyeball, and $$D - P = (A - \rho) \times \sin\theta \quad (3)$$

is obtained. At this time, if it is supposed that the angle θ of rotation of the eyeball 1 is small, then, by postulating that sin θ is approximately equal to θ, the angle θ of rotation of the eyeball 1 can be calculated by rewriting the above equation (3) to give:

$$\theta = \frac{D - P}{A - \rho} \quad (4)$$

Since the distance D-P can be measured from the image reflected from the eyeball 1, therefore the angle θ of rotation of the eyeball 1 can be calculated by substituting an appropriate constant for the distance A-ρ.

Nevertheless, with the visual line detection device disclosed in the above described publication, a problem arises in connection with the fact that the equations (1) through (3) essentially only hold for a reflected image from the cornea focused from parallel light rays. Because in practice the calculations for visual line detection are performed using these equations (1) to (3) for a light source for visual line detection which is at a finite distance and not at infinity, the problem arises of a risk that deviation of the obtained visual line from the actual visual line of the observer can occur. This will be explained with reference to FIGS. 31(A)–31(C).

FIG. 31(A) shows the case where parallel light rays PL from a light source S at infinity are squarely incident upon the front face of the eyeball 1, and the image P reflected from the cornea 6 is generated at a position at a distance exactly r/2 towards the light source (at infinity) from the center C of curvature of the cornea (r is the radius of curvature of the cornea 6); and moreover the center O' of rotation of the eyeball 1, the center C of curvature of the cornea 6, and the image P reflected from the cornea 6 are all collinear. If however this light source S is positioned at a finite distance as shown in FIG. 31(B), then due to the fact that the light rays from this light source S at a finite distance are diverging light rays DL, the image P' reflected from the cornea 6 is generated at a position displaced exactly Δr towards the light source S, as compared to the above described case of parallel light rays PL. Further, if as shown in FIG. 31(C) the eyeball 1 is displaced in parallel in the downwards direction as seen in the figure by exactly a distance L, then the image P' reflected from the cornea 6 is generated at a position displaced angularly around the center C of curvature of the cornea 6 by exactly an angle α, displaced Δr' towards the light source, and as seen from the front is displaced by exactly ΔL in the upwards direction as seen in the figure. On the other hand, if parallel light rays PL were to be incident squarely upon the front face of the eyeball 1, even if as shown in FIG. 31(C) the eyeball 1 were subjected to parallel displacement, the image reflected from the cornea 6 would still be generated at the position P'. Accordingly, ΔL is the amount of deviation due to the light source S being positioned at a finite distance.

SUMMARY OF THE INVENTION

An objective of the present invention is to provide a visual line detection means which can accurately determine the direction of the visual line of an eyeball even when using light sources disposed at positions which cannot be assumed to be at infinity, and to provide a camera equipped with such a visual line detection means.

In order to attain this objective, the present invention proposes a visual line detection device which calculates the direction of the visual line of the eyeball of an observer according to image reflection from said eyeball, comprising: a plurality of illumination means which illuminate said eyeball of said observer; and a visual line calculating means which determines the position of the center of curvature of the cornea of said eyeball based upon images reflected from the cornea of said eyeball which are generated by light rays from said plurality of illumination means, and calculates the direction of said visual line using said position of the center of curvature of said cornea of said eyeball.

And, moreover, the present invention proposes a visual line detection device which calculates the direction of the visual line of the eyeball of an observer according to image reflection from said eyeball, comprising: a plurality of illumination means which illuminate said eyeball of said observer; a cornea reflected image position calculating means which calculates the positions of images reflected from the cornea of said eyeball which are generated by light rays from said plurality of illumination means; a cornea center of curvature position calculating means which determines the position of the center of curvature of said cornea of said eyeball based upon the positions of said images reflected from said cornea and upon the positions of said plurality of illumination means; and a visual line calculating means which calculates the direction of said visual line based upon said position of the center of curvature of said cornea of said eyeball.

Further, in order to attain the above defined objective, the present invention proposes a camera, comprising: a viewfinder device which comprises a viewfinder eyepiece; and a visual line detection device, which calculates the direction of the visual line of the eyeball of an observer looking through said viewfinder eyepiece according to image reflection from said eyeball, comprising: a plurality of illumination means which illuminate said eyeball of said observer; and a visual line calculating means which determines the position of the center of curvature of the cornea of said eyeball based upon images reflected from the cornea of said eyeball which are generated by light rays from said plurality of illumination means, and calculates the direction of said visual line using said position of the center of curvature of said cornea of said eyeball.

And, moreover, the present invention proposes a camera, comprising: a viewfinder device which comprises a viewfinder eyepiece; and a visual line detection device, which calculates the direction of the visual line of the eyeball of an observer looking through said viewfinder eyepiece according to image reflection from said eyeball, comprising: a plurality of illumination means which illuminate said eyeball of said observer; a cornea reflected image position calculating means which calculates the positions of images reflected from the cornea of said eyeball which are generated by light rays from said plurality of illumination means; a cornea center of curvature position calculating means which determines the position of the center of curvature of said cornea of said eyeball based upon the positions of said images reflected from said cornea and upon the positions of said plurality of illumination means; and a visual line calculating means which calculates the direction of said visual line based upon said position of the center of curvature of said cornea of said eyeball.

A fixed relationship holds between the positions of the images reflected from the cornea of the eyeball which are generated by light rays from the plurality of illumination means, the position of the center of curvature of the cornea of the eyeball, and the positions of the plurality of illumination means; and this is a function which depends upon the distance between the illuminating means and the positions of the images reflected from the cornea of the eyeball. According to the present invention, since at least two illuminating means are provided, and since the positions of the plurality of images reflected from the cornea of the eyeball which are generated by light rays from these plurality of illuminating means are determined, simultaneous equations can be set up by considering the above relationships which hold for each of said plurality of images reflected from the cornea, and the distance between the illuminating means and the positions of the images reflected from the cornea of the eyeball, taken as a variable, can be eliminated from these simultaneous equations; and thereby it is possible directly to obtain the position of the center of curvature of the cornea of the eyeball, which is necessary for obtaining the direction of the visual line. Accordingly, since it is possible directly to obtain the position of the center of curvature of the cornea of the eyeball, even when the illumination means are at a finite distance, it is possible accurately to determine the visual line of the eyeball of the observer.

Being able to dispose the illumination means at a position which is at a finite distance has the following advantages. In the prior art, because it was necessary to illuminate the eyeball of the observer with parallel light rays in order accurately to perform detection of the visual line of said eyeball, it was desirable to dispose the illumination means in the plane of view of the observer by using an optical system including a half mirror or the like. This method of disposition of the illumination means was liable to present the problem of limiting the freedom in location for the illumination means and of ghosting and the like within this optical system. However, according to the present invention, since it is possible accurately to determine the visual line of the eyeball of the observer even when the illumination means are positioned at a finite distance, even if the eyeball of the observer is directly illuminated by the illumination means without the use of any optical system, it is possible to determine the direction of the visual line of the observer, and it is possible to avoid the generation of optical system ghosts and the like since no optical system needs to be used, and accordingly it is possible to perform accurate visual line detection. Additionally, it is possible to improve the freedom in location for the illumination means. The same advantages are also obtained in the case that the light receiving means is provided in a position which can directly receive the images reflected from the eyeball.

BRIEF DESCRIPTION OF THE DRAWINGS

FIGS. 8A and 8B are flow charts for explanation of the operation of the first embodiment of the present invention;

FIGS. 15A and 15B are flow charts for explanation of the operation of the second embodiment of the present invention;

FIG. 16 is a flow chart which continues directly on from the FIG. 15 flow chart;

DESCRIPTION OF THE PREFERRED EMBODIMENT

In the following, several embodiments of the present invention will be described with reference to the drawings. Moreover, when in the following discussions explanations are being provided with regard to the eyeball of the observer and the internal structures thereof, the same reference symbols will be used as were used above in the discussion relating to FIGS. 30 and 31(A)–31(C).

First Embodiment (in which exactly two light sources are used)

In the following, a first embodiment will be explained in which exactly two light sources for visual line detection are provided.

(1) Structure of the Visual Line Detection Device

Figure 1:
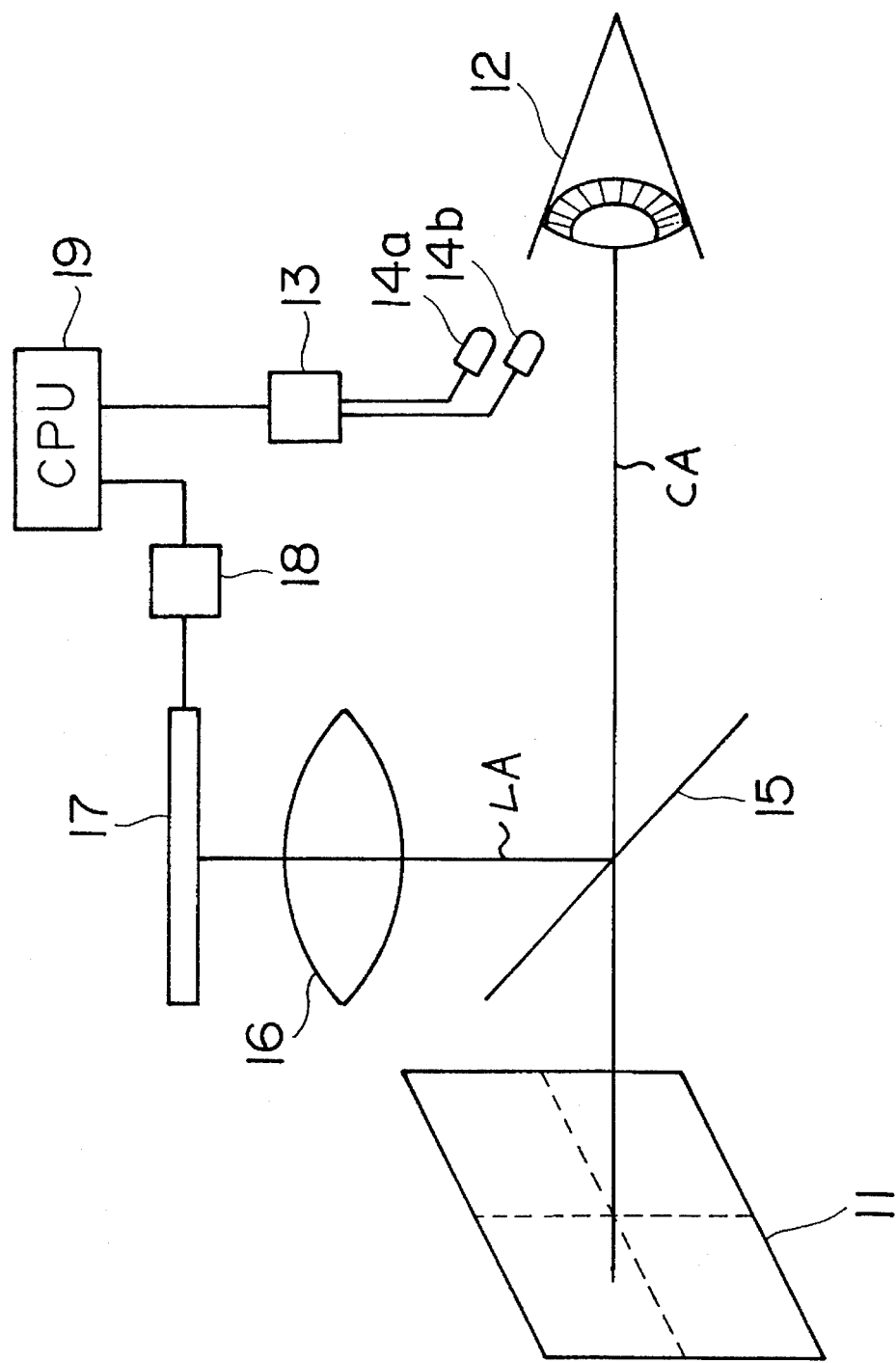
FIG. 1 is a figure showing the general construction of a visual line detection device which is the first embodiment of the present invention.

FIG. 1 is a figure showing the general construction of the first embodiment of the visual line detection device of the present invention, and in this figure the reference numeral 11 denotes a field of observation 11 provided within an optical device such as a camera or the like, and an observer is shown as fixating his or her attention upon a special point (called the fixation point) within this field of observation 11. 12 denotes the eyeball of the observer, 13 denotes a visual line detection light source drive means, and 14a and 14b both are light sources for visual line detection. These light sources for visual line detection 14a and 14b are disposed in close proximity to the eyeball 12 of the observer and are arranged at positions in the field of view which do not obstruct the field of observation 11 which this eyeball 12 of the observer is observing. Moreover, these two light sources 14a and 14b will be referred to collectively by the symbol 14 when there is no intention particularly to distinguish them from one another, but only to refer to them collectively as a unitary light source means.

Figure 30:
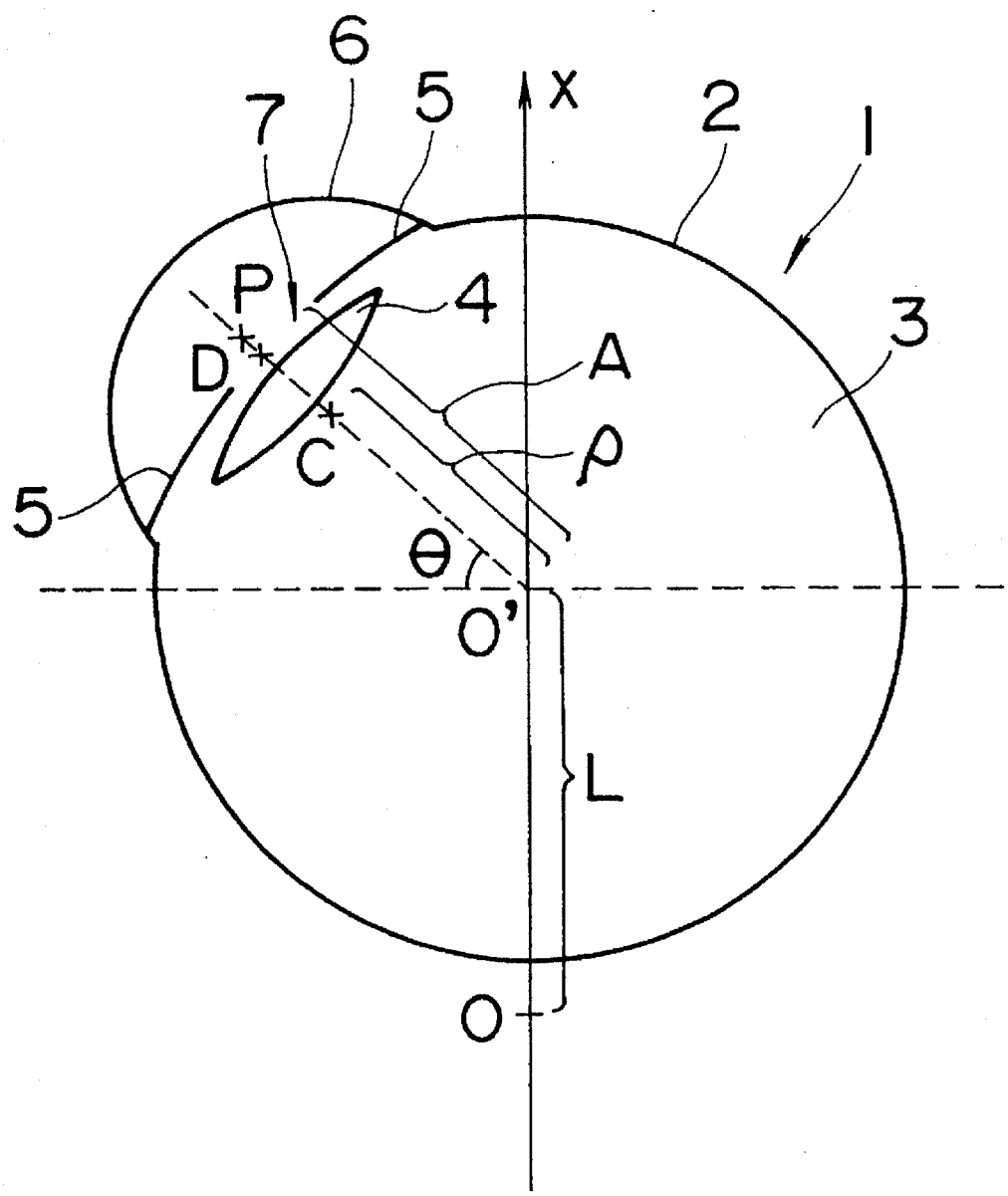
FIG. 30 is a sectional view taken through a human eyeball in a horizontal plane.
Figure 31:
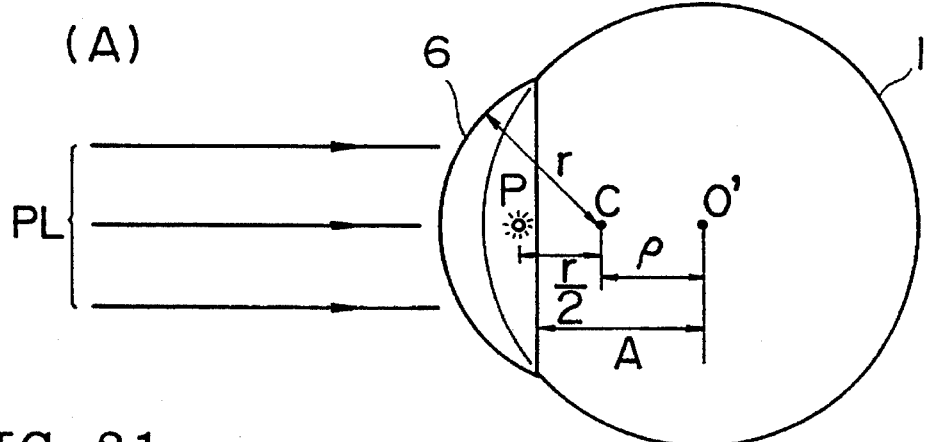
FIGS. 31(A) through 31(C) are figures showing a sectional view of a human eyeball, particularly for explanation of the deviation of the position of an image reflected from the cornea, when the incident light rays are diverging light rays, from its position when the incident light rays are parallel light rays.
Figure 31:
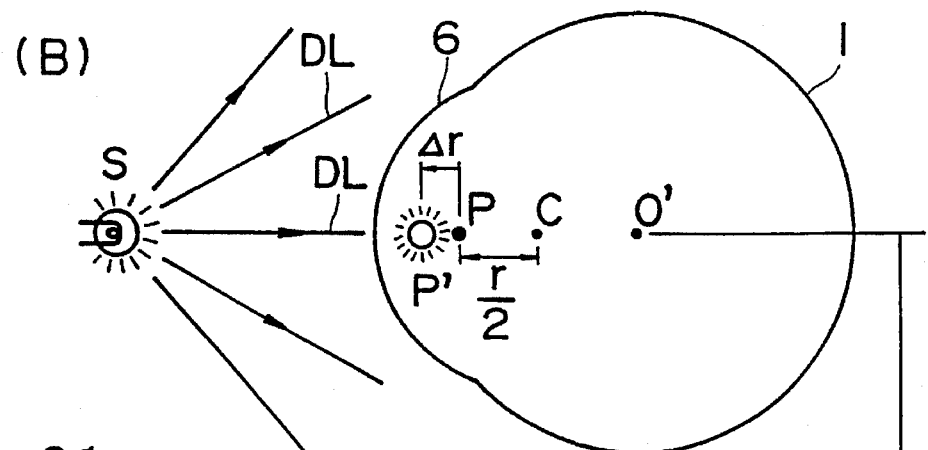
Figure 31:
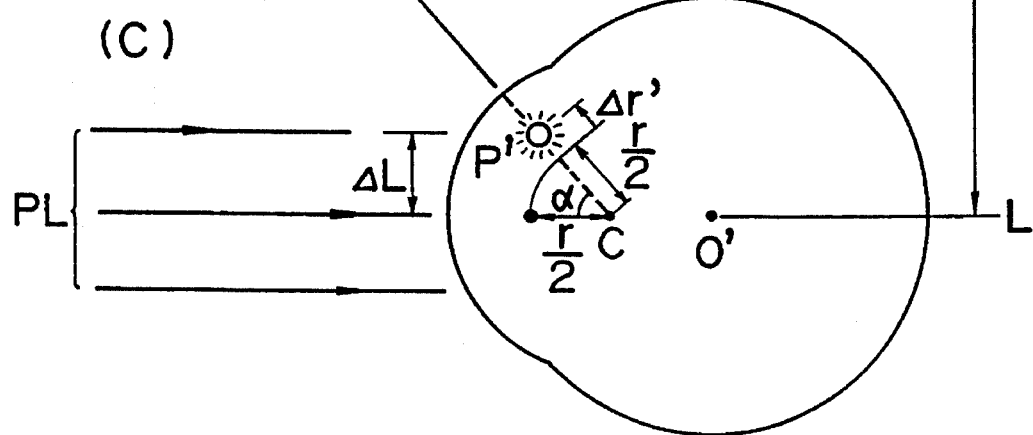

15 is a dichroic mirror which passes the visible region of the spectrum but reflects the infrared region, 16 is a converging lens, and 17 is a photoelectric conversion device; and the optical axis LA of this converging lens 16 and of this photoelectric conversion device 17, when bent by said dichroic mirror 15, passes through the central point of the field of observation 11 and through the origin point 0 as shown in FIG. 30 (which agrees with the center O' of rotation of the eyeball 1 when said eyeball 1 is in a position squarely against the center of a plane of view, not particularly shown in the figure) and optically coincides with the axis CA; and moreover, since this optical axis LA is bent by the dichroic mirror 15, the converging lens 16 and the photoelectric conversion device 17 are arranged at positions in the field of view which do not obstruct the field of observation 11 which is being observed. 18 denotes a signal processing means which processes the output of the photoelectric conversion device 17, and 19 is a calculation device, and this calculation device 19 performs the control of the visual line detection light source drive means 13 and also controls the driving of the photoelectric conversion device 17, and determines the visual line from the output of the signal processing means 18.

Figure 2:
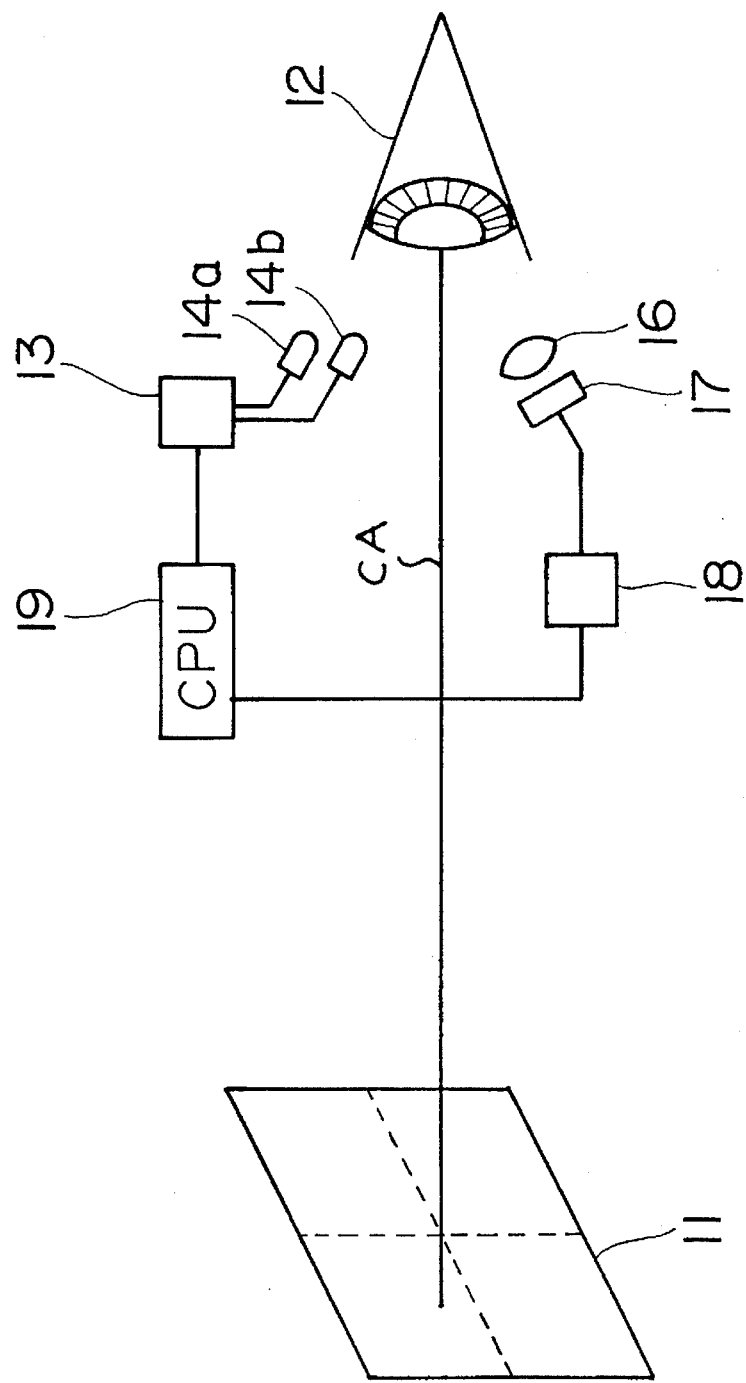
FIG. 2 is a figure showing another example of construction of a visual line detection device according to the first embodiment.

FIG. 2 is a constructional figure showing another possible arrangement of the light sources 14 for visual line detection and the photoelectric conversion device 17, according to a variant of the first embodiment of the present invention. In the example shown in FIG. 2, no dichroic mirror such as the dichroic mirror 15 of FIG. 1 is provided, and the converging lens 16 and the photoelectric conversion device 17 are disposed in positions which do not optically correspond to the axis CA which passes from the eyeball 12 of the observer through the center of the field of observation 11.

Figure 3A:
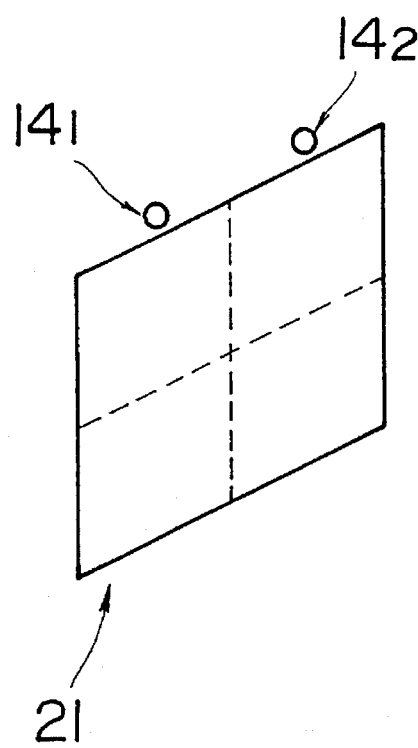
FIGS. 3(A) through 3(B) are figures showing an example of the disposition of the light sources for visual line detection in the first embodiment.

FIGS. 3(A) and (B) are figures showing, when the eyeball 12 of the observer is at a position squarely against the center of the field of observation 11, the disposition of the light sources 14 for visual line detection as seen by this eyeball 12 of the observer when observing the field of observation 11.

Figure 4:
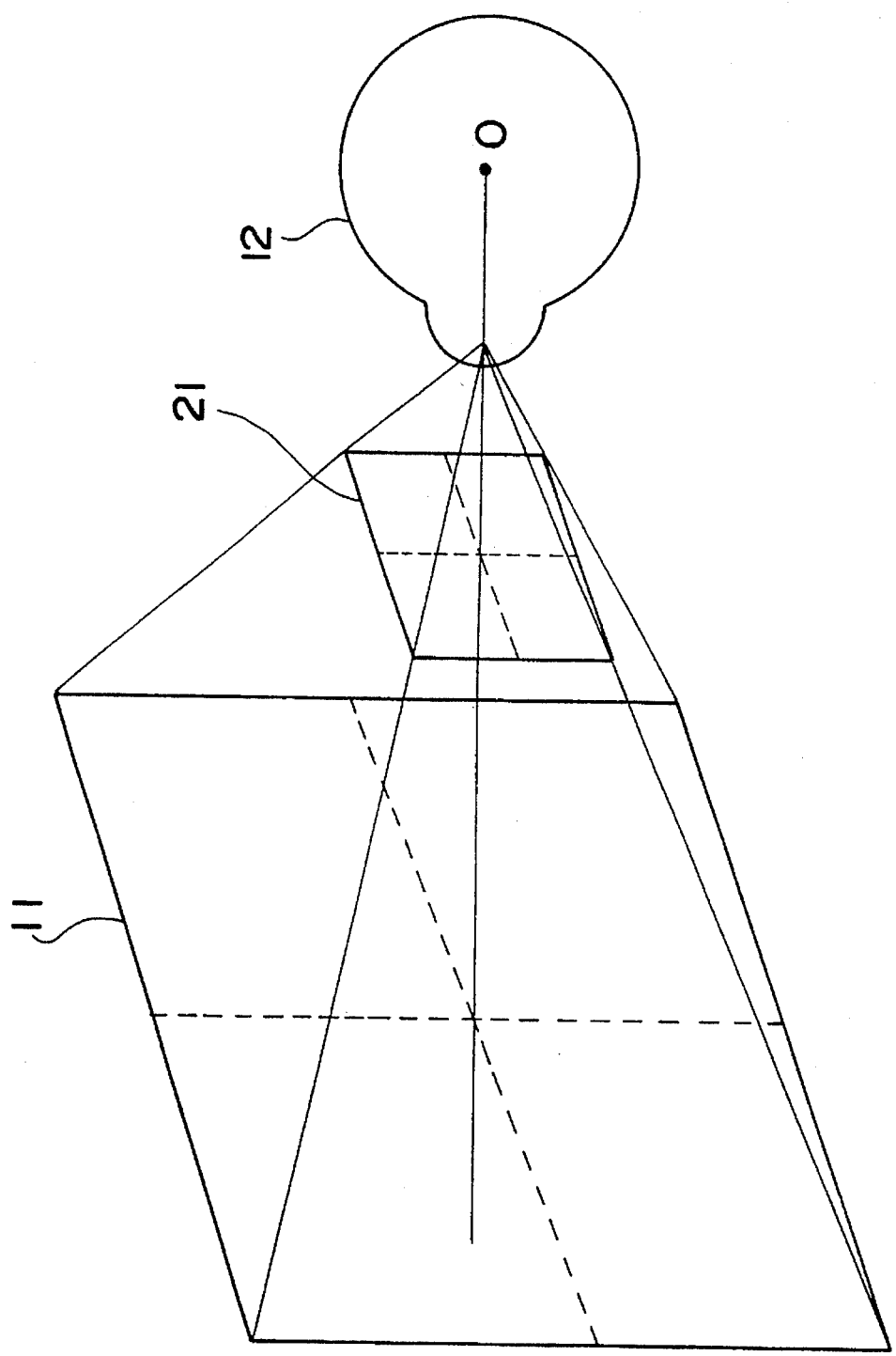
FIG. 4 is a figure displaying the relationship between the field of observation and the visual field frame.

The frame 21 in the figures is, as shown in FIG. 4, a hypothetical frame which delimits the range of the field of observation 11 when the eyeball 12 of the observer is at a position squarely against the center of the field of observation 11, and it has a field of view equal to the field of observation 11. This frame 21 will be termed the "visual field frame" in the following disclosure. This visual field frame 21 can be set equally well in any position from directly in front of the eyeball 12 of the observer to right up against the field of observation 11, since it is a frame which delimits the frame observed by the eyeball 12 of the observer.

Figure 3B:
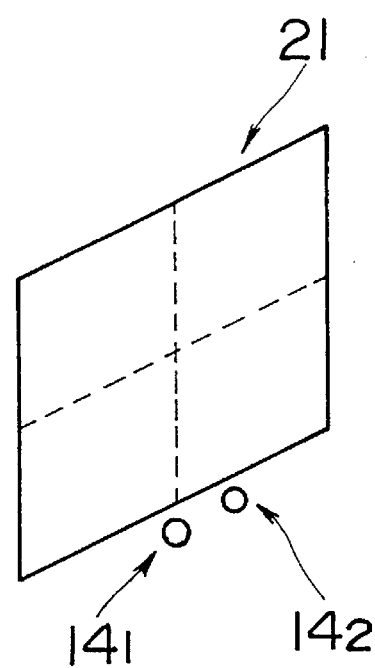

In FIGS. 3(A) and 3(B), two light sources 14 for visual line detection are used: IRED14$_1$ and IRED14$_2$ (the term "IRED" is an acronym for "Infra-Red Emitting Diode"). IRED14$_1$ and IRED14$_2$ are disposed in positions so that a straight line joining IRED14$_1$ and IRED14$_2$ does not overlap the visual field frame 21, and in concrete terms the two light sources IRED14$_1$ and IRED14$_2$ are disposed on the outer periphery of the visual field frame 21. Providing that the center C of curvature of the cornea 6 of the eyeball 12 of the observer is within the visual field frame 21, it is therefore guaranteed that this center C of curvature of the cornea 6 is not positioned on the straight line joining IRED14$_1$ and IRED14$_2$, and therefore as described hereinafter it is possible to prevent it ever being impossible to determine the visual line of the observer.

FIG. 3(A) is a figure showing an example in which the two light sources IRED14$_1$ and IRED14$_2$ are disposed along the upper portion of the periphery of the visual field frame 21, and, when the horizontal direction of the visual field frame 21 is taken as the X axis and its vertical direction is taken as the Z axis, then the values of the coordinates (Sx, Sz) of the IREDs 14 satisfy $Sx_1=-Sx_2$ and $Sz_1=Sz_2$. In the same manner, FIG. 3(B) is a figure showing an example in which the two light sources IRED14$_1$ and IRED14$_2$ are disposed along the lower portion of the periphery of the visual field frame 21, and the values of the coordinates (Sx, Sz) of the IREDs 14 satisfy $Sx_1=0$ and $Sz_1=Sz_2$. It should be understood that the disposition of IRED14$_1$ and IRED14$_2$ is not to be considered as being limited to the examples shown in this figure; it would be acceptable to dispose these two IREDs in various other configurations, as long as they were in the neighborhood of the eyeball 12 of the observer.

(2) Explanation of the Coordinate Systems

Figure 6:
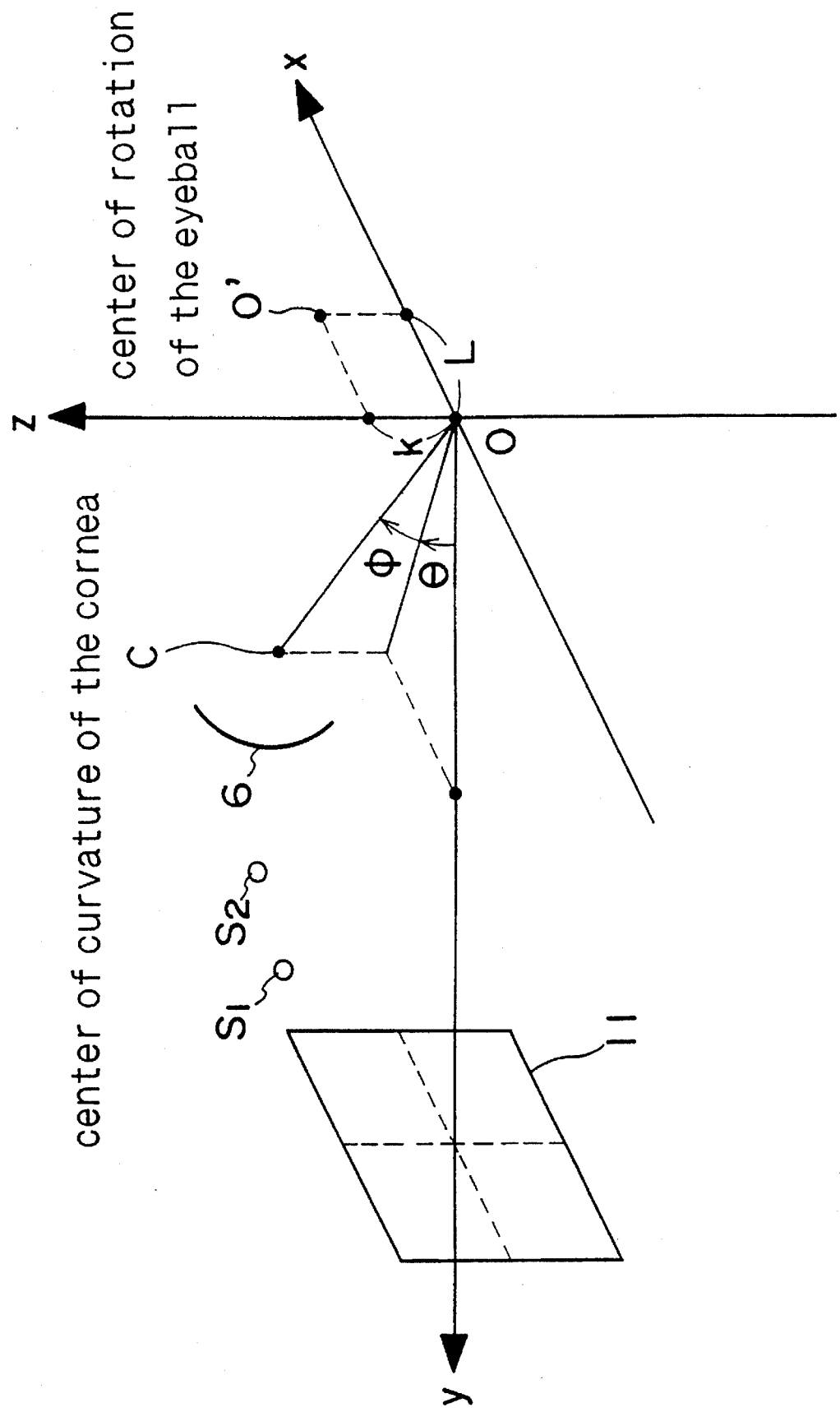
FIG. 6 is a figure showing a coordinate system for explanation of the theory of the present invention.

FIG. 6 is a figure showing a coordinate system for introduction of an explanation of the theory of the present invention. Referring to FIG. 6, three dimensional coordinates will be established with the position O' of the center of rotation of the eyeball of the observer when the eyeball is at a position squarely against the center of the plane of observation being taken as the origin 0, the axial direction from this origin 0 to the central point of the field of observation 11 being taken as the Y axis, a direction along the field of observation 11 being taken as the X axis, and the direction along the field of observation 11 perpendicular to both this X axis and this Y axis being taken as the Z axis; and this coordinate system will hereinafter be termed "actual space coordinates".

Figure 5:
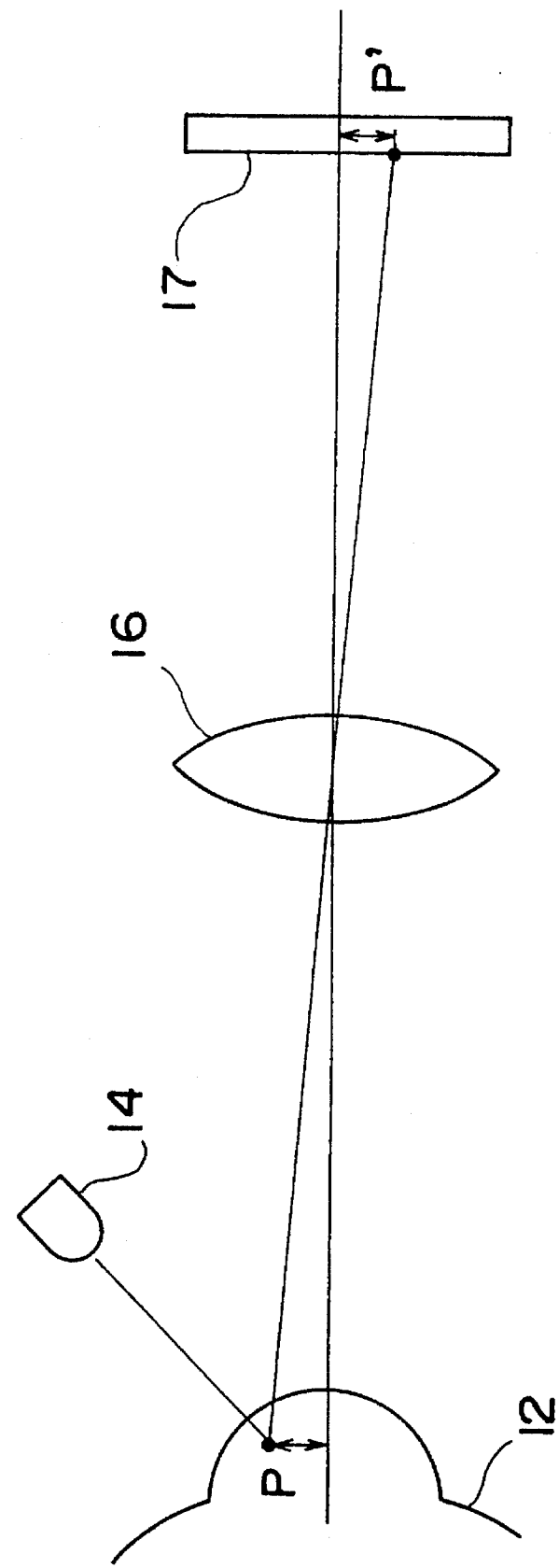
FIG. 5 is a figure showing the optical system of the present invention.

FIG. 5 is a view showing the optical theory of the present invention. The light sources 14 for visual line detection are disposed in close proximity to the eyeball 12 of the observer, and light ray from a one 14 of these light sources 14 is reflected from the cornea of the eyeball 12 of the observer so as to be focused as a virtual image at a point P. This virtual image is again brought to a focus, via the focusing lens 16, at a point P' on the photoelectric conversion device 17. At this time, three dimensional coordinates will be established with one direction along the light receiving face of the photoelectric conversion device 17 being taken as the X' axis, and the direction on said light receiving face perpendicular to this X' axis being taken as the Z' axis; and this coordinate system will hereinafter be termed "observation plane coordinates". The point P is given in actual space coordinates by (Px, Py, Pz), while the point P' is given in observation plane coordinates as (Px', Pz'). If the functions fx and fz are used for the relationship between the point P and the point P', taking into account the angle with respect to the actual space coordinate system of the light receiving face of the photoelectric conversion device, i.e. the angle of the observation plane coordinate system with respect to the actual space coordinate system, so that:

$$Px=f_x(Px', Pz') \tag{5}$$

$$PZ=f_z(PX',PZ') \tag{6}$$

then it is possible to convert any set of coordinates in the observation plane coordinate system into a set of coordinates in the x–z plane of the actual space coordinate system. Hence, when observations are made on the light receiving surface of the photoelectric conversion device 17, and pairs of coordinates in the observation plane coordinate system are obtained for the image point P' reflected from the cornea and focused on the photoelectric device 17 and for the point representing the position of the central point of the pupil on said photoelectric conversion device 17, both these pairs of coordinates in the observation plane coordinate system can be converted into pairs of coordinates in the x–z plane of the actual space coordinate system. Or, to put it in another way, the coordinates of image points focused on the photoelectric conversion device 17 can be converted into x–z plane coordinates in the actual space coordinate system by using the conversion equations (5) and (6). As described above, even if the positional relationships between the point P, the converging lens 16, and the photoelectric device 17 change, only the concrete forms of the equations (5) and (6) change, and there is no change in the fact that it is possible to convert between the coordinates of the point P and the coordinates of the point P' by using the equations (5) and (6).

(3) Explanation of the Theory of Visual Line Detection

Figure 7:
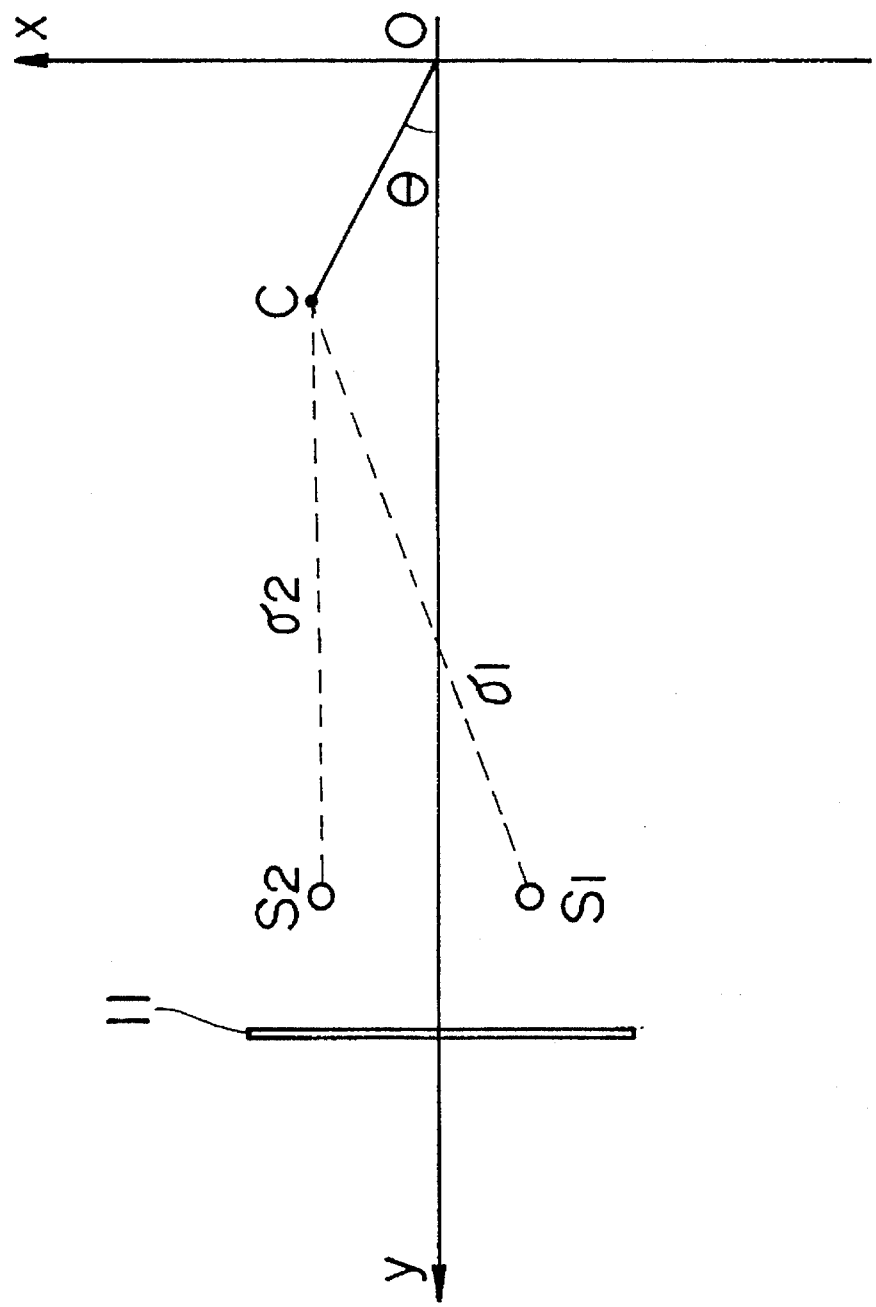
FIG. 7 is another figure for explanation of the theory of the present invention.

Next, the theory of the visual line detection procedure employed in the present invention will be explained with the use of the previously discussed actual space coordinate system, while taking due account of the fact that the light sources 14 for visual line detection used in the present invention for illuminating the eyeball of the observer are point light sources at a finite distance, so that they illuminate the eyeball with divergent light. As shown in FIG. 6 and FIG. 7, the values $(X_{p1}, Y_{p1}, Z_{p1})$ of the coordinates in the actual space coordinate system of the first Purkinje image P generated by a light source 14 and the values (Xd, Yd, Zd) of the coordinates of the center D of the pupil are obtained as shown in the following equations, using the values (Sx, Sy, Sz) of the coordinates of the light source S and the values (Cx, Cy, Cz)=$(L+\rho \cos\Phi \sin\theta, \rho\cos\Phi\cos\theta, k+\rho\sin\Phi)$ of the coordinates of the center C of curvature of the cornea 6. In these equations, f is the focal length of the reflecting surface of the cornea 6, $\rho$ is the distance between the center of rotation of the eyeball 1 and the center of curvature of the cornea 6, L is the distance of parallel displacement along the X axis of the center of rotation of the eyeball 1, $\Phi$ is the angle of rotation of the eyeball 1 in the X axis direction, k is the distance of parallel displacement along the Z axis of the center of rotation of the eyeball 1, and $\Phi$ is the angle of rotation of the eyeball in the Z axis direction. First, the values of the coordinates of the first Purkinje image are given by:

$$X1_{p1} = \frac{f}{\sigma_1 - f} Sx_1 + \left(1 - \frac{f}{\sigma_1 - f}\right) Cx \tag{7}$$

$$Z1_{p1} = \frac{f}{\sigma_1 - f} Sz_1 + \left(1 - \frac{f}{\sigma_1 - f}\right) Cz \tag{8}$$

$$X2_{p1} = \frac{f}{\sigma_2 - f} Sx_2 + \left(1 - \frac{f}{\sigma_2 - f}\right) Cx \tag{9}$$

$$Z2_{p1} = \frac{f}{\sigma_2 - f} Sz_2 + \left(1 - \frac{f}{\sigma_2 - f}\right) Cz \tag{10}$$

However, $$\sigma_1 = \sqrt{(Sx_1 - Cx)^2 + (Sy_1 - Cy)^2 + (Sz_1 - Cz)^2} \tag{11}$$

$$\sigma_2 = \sqrt{(Sx_2 - Cx)^2 + (Sy_2 - Cy)^2 + (Sz_2 - Cz)^2} \tag{12}$$

also hold. Here, $\sigma_1$ denotes the distance between the light source S1 and the center C of curvature of the cornea, and $\sigma_2$ denotes the distance between the light source S2 and the center C of curvature of the cornea. Considering $\sigma_1$ and $\sigma_2$ as the variables in equations (7) through (10) above, obtaining the values of the coordinates of the center C of curvature of the cornea 6 gives:

$$Cx = \frac{Sx_1 Z1_{p1}(Sx_2 - X2_{p1}) - Sx_2 Z2_{p1}(Sx_1 - X1_{p1}) - Sz_1 X1_{p1}(Sx_2 - X2_{p1}) + Sz_2 X2_{p1}(Sx_1 - X1_{p1})}{(Sx_1 - X1_{p1}) \times (Sz_2 - Z2_{p1}) - (Sx_2 - X2_{p1}) \times (Sz_1 - Z1_{p1})} \tag{13}$$

$$Cz = \frac{Sz_1 X1_{p1}(Sz_2 - Z2_{p1}) - Sz_2 Z2_{p1}(Sz_1 - Z1_{p1}) - Sx_1 Z1_{p1}(Sz_2 - Z2_{p1}) + Sx_2 Z2_{p1}(Sz_1 - Z1_{p1})}{(Sz_1 - Z1_{p1}) \times (Sx_2 - X2_{p1}) - (Sz_2 - Z2_{p1}) \times (Sx_1 - X1_{p1})} \tag{14}$$

On the other hand, the values of the coordinates (Cx, Cz) of the center C of curvature of the cornea 6 are given, as described above, by:

$$Cx = L + \rho\cos\Phi\sin\theta \tag{13'}$$

$$Cz = k + \rho\sin\Phi \tag{14'}$$

Further, the values of the coordinates (Xd, Zd) of the central point D of the pupil are given, if the distance from the center O' of rotation of the eyeball to the central point D of the pupil is denoted by A, by:

$$Xd = L + A\cos\Phi\sin\theta \tag{15}$$

$$Zd = k + A\sin\Phi \tag{16}$$

If the above equations (13'), (14'), (15), (16) are solved simultaneously, then $\theta$, L, $\Phi$, and k can be determined and the direction of the visual line can thus be obtained, in the following manner:

$$\theta = \sin^{-1} \frac{Xd - Cx}{(A - \rho)\cos\left(\sin^{-1} \frac{Zd - Cz}{A - \rho}\right)} \tag{17}$$

$$L = -\frac{\rho}{A - \rho} Xd + \frac{A}{A - \rho} Cx \tag{18}$$

$$\phi = \sin^{-1} \frac{Zd - Cz}{A - \rho} \tag{19}$$

$$k = -\frac{\rho}{A - \rho} Zd + \frac{A}{A - \rho} Cz \tag{20}$$

Here particular attention should be paid to the point that, when the center C of curvature of the cornea 6 lies on the straight line joining the first light source S1 and the second light source S2, the denominator of the equations (13) and (14) becomes zero, so that the calculation then becomes impossible. Accordingly, it is necessary to plan the positions for disposition of the light sources S1 and S2 appropriately.

(4) The Actual Procedure for Calculation

In the following, the concrete procedure for deriving the values (Cx, Cz) of the coordinates of the position of the center C of curvature of the cornea 6 of the observer and the values (Xd, Zd) of the coordinates of the position of the center D of the pupil will be explained.

Figure 8B:
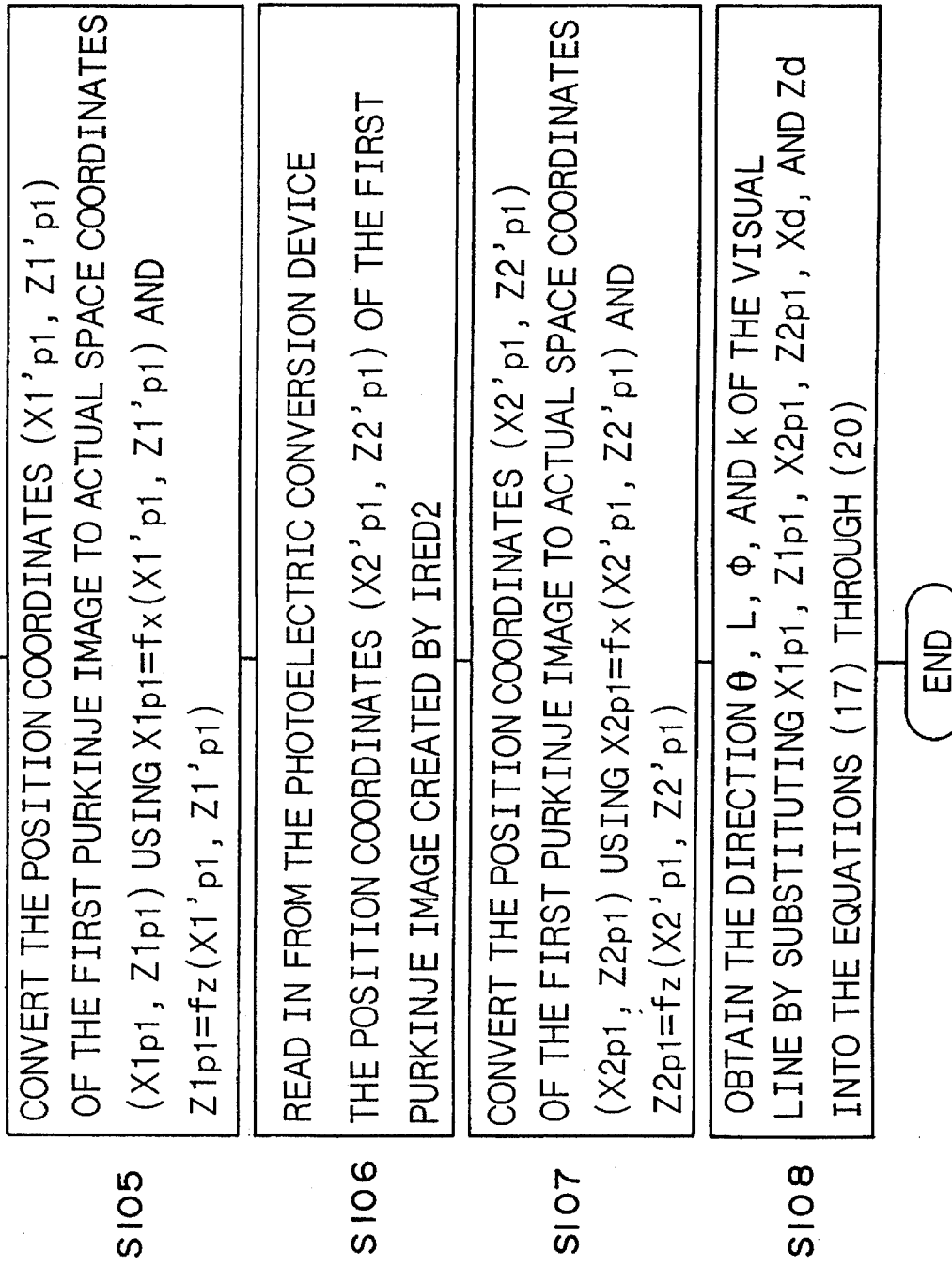

FIGS. 8A and 8B are flow charts showing the process of visual line detection calculation as performed by the visual line detection device of this first preferred embodiment. First, in the step S101, the eyeball 12 of the observer is illuminated by IRED14$_1$ and IRED14$_2$, which are the pair of light sources 14 for visual line detection, and the boundary between the pupil 7 and the iris 5 of the eyeball 1 thus illuminated by this IRED14$_1$ and IRED14$_2$ is read in as the values $(x'_{dL}, z'_{dL})$ and $(x'_{dR}, z'dr)$ of the coordinates of two points on the photoelectric conversion device 17. For example, the two points are located at right and left side points of the boundary between the pupil 7 and the iris 5 of the eyeball 1, respectively. The details of this boundary detection procedure will not be explained herein at length because they are per se well known in the art, and can be found, for example, in the previously cited Japanese Patent Laid-Open Publication Heisei 3-109029. Next, in the step S102, the values $(x'_{dL}, z'_{DL})$ and $(x'_{dR}, z'_{dR})$ of the coordinates of the two points on the photoelectric conversion device 17 which were read in the step S101 are converted into actual space coordinates, so as to obtain the values $(x_{dL}, Z_{dL})$ and $(X_{dR}, Z_{dR})$ for the coordinates of the boundary between the pupil 7 and the iris 5 in the actual space coordinate system. Next, in the step S103, the central point of a straight line connecting the two points of the boundary between the pupil 7 and the iris 5 in actual space is taken as the position of the center D of the pupil 7, and the values (Xd, Zd) of the coordinates of this center D of the pupil 7 are determined.

Next, in the step S104, the position of the first Purkinje image P1 (the image reflected from the cornea 6) generated by the illumination with divergent light rays emanating from IRED141, which is the first light source for visual line detection, is detected as values $(X1'_{p1}, Z1'_{p1})$ of the coordinates on the photoelectric conversion device 17. The details of this first Purkinje image detection procedure will not be explained herein at length because they are also per se well known in the art. Next, in the step S105 the values $(X1'_{p1}, Z1_{p1})$ of the coordinates of the first Purkinje image on the photoelectric conversion device 17 are converted into actual space coordinate values, so as to obtain the values $(X1_{p1}, Z1_{p1})$ of the coordinates of the first Purkinje image in the actual space coordinate system.

In the same manner, in the next step S106, the position of the first Purkinje image P2 (the image reflected from the cornea 6) generated by the illumination with divergent light rays emanating from IRED14$_2$, which is the second light source for visual line detection, is detected as values $(X2'_{p1}, Z2'_{p1})$ of the coordinates on the photoelectric conversion device 17. Next, in the step S107, the values $(X2'_{p1}, Z2'_{p1})$ of the coordinates of the first Purkinje image P2 on the photoelectric conversion device 17 are converted into actual space coordinate values, so as to obtain the values $(X2_{p1}, Z2_{p1})$ of the coordinates of the first Purkinje image P2 in the actual space coordinate system.

Next, in the step S108, by substituting the values $(X1_{p1}, Z1_{p1})$ and $(X2_{p1}, Z2_{p1})$ of the coordinates of the first Purkinje images P1 and P2 and the values (Sx1, Sz1) and (Sx2, Sz2) of the coordinates of the light sources S1 and S2 into the equations (13) and (14), the values (Cx, Cz) of the coordinates of the center C of curvature of the cornea 6 are obtained; and then, by substituting the values (Cx, Cz) of the coordinates of this center C of curvature of the cornea 6 and the values $(X1_{p1}, Z1_{p1})$ and $(X2_{p1}, Z2_{p1})$ of the coordinates of the first Purkinje images P1 and P2 and the values (Xd, Zd) of the coordinates of the center D of the pupil into the equations (17) through (20), the values θ, L, Φ, and k which together determine the visual line of the observer are obtained. In this process, although the unknown variables A and ρ enter into the equations (17) through (20), it will be acceptable to substitute appropriate values for them and thus to treat them as constant values, since these values do not vary much.

By using the above procedure, the position of the center C of curvature of the cornea 6 can be directly determined, and then the values of θ, L, Φ, and k which together determine the visual line of the eyeball 12 of the observer can be accurately obtained by using this position of the center C of curvature of the cornea 6.

Second Embodiment (in which three or more light sources are used)

In the following, a second embodiment will be explained in which at least three light sources for visual line detection are provided.

As described above, if the center C of curvature of the cornea 6 of the eyeball 12 of the observer should happen to be positioned on the straight line joining the two light sources for visual line detection 14a and 14b, then it is not possible to determine the position of the center C of curvature of the cornea 6 according to the theory of the present invention. Therefore, in this second embodiment of the present invention, at least three light sources for visual line detection are provided, and then, when the center C of curvature of the cornea of the eyeball 12 of the observer is positioned on the straight line joining any two of these light sources for visual line detection, visual line detection is performed by using a different combination of the light sources for visual line detection, for which combination the center C of curvature of the cornea is not positioned on the straight line joining them. Accordingly, it is not desirable for all of the light sources for visual line detection to lie on the same straight line; indeed, it is desirable that no single one of the light sources for visual line detection should lie on any of the straight lines joining any other two of said light sources for visual line detection.

Figure 9:
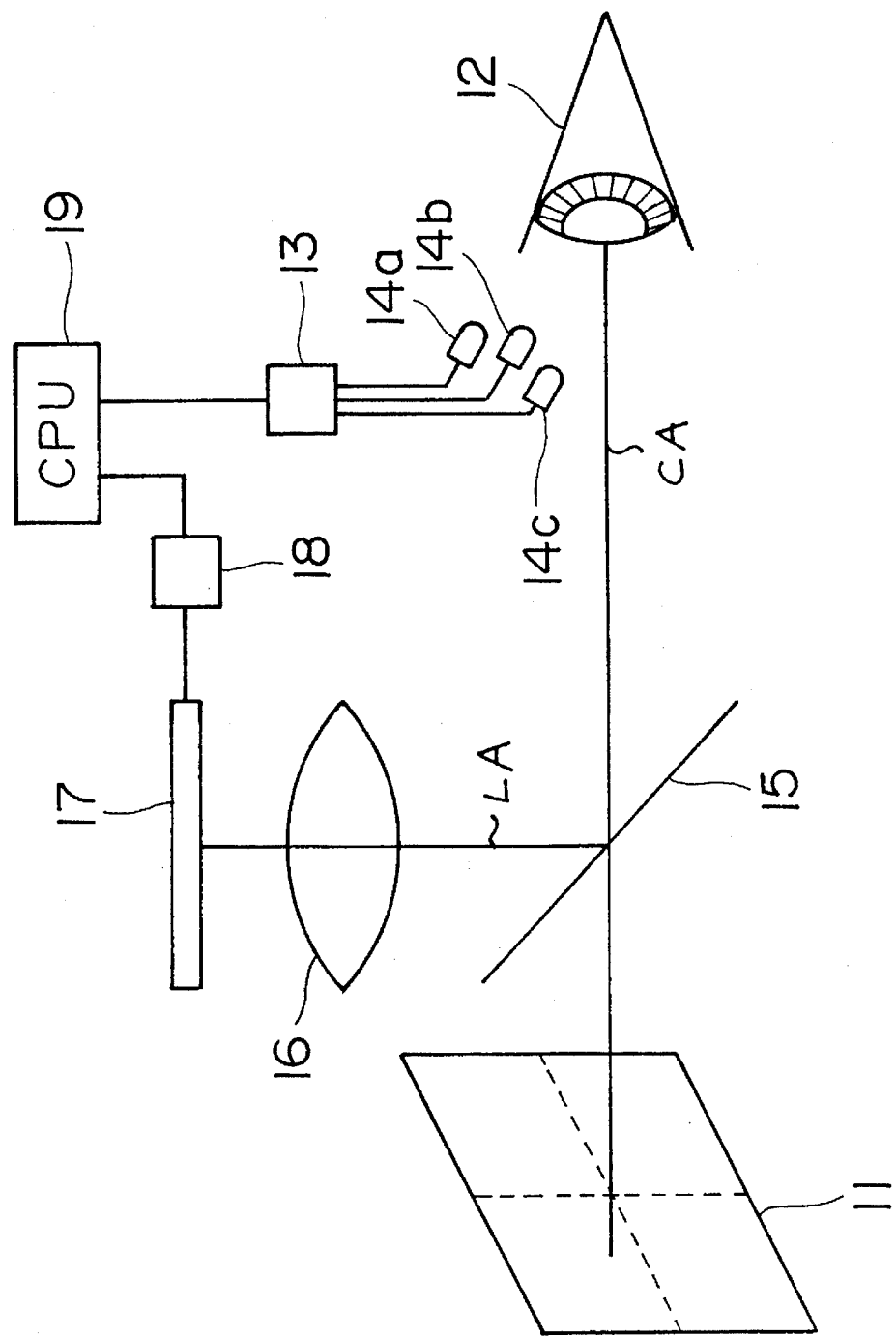
FIG. 9 is a figure showing the general construction of a visual line detection device which is the second embodiment of the present invention.

FIG. 9 is a figure showing the general construction of the second embodiment of the visual line detection device of the present invention. In the following explanation and in the figures, elements of the construction of this second embodiment which are identical to ones in the above described first embodiment the same reference symbols are identified with similar reference numbers, and description thereof will be omitted or abbreviated in the interests of conciseness of disclosure.

In the device shown in FIG. 9, three light sources for visual line detection 14a through 14c are used, and these three light sources for visual line detection 14a through 14c are disposed in close proximity to the eyeball 12 of the observer and are arranged at positions in the field of view which do not obstruct the field of observation 11 which this eyeball 12 of the observer is observing.

Figure 10:
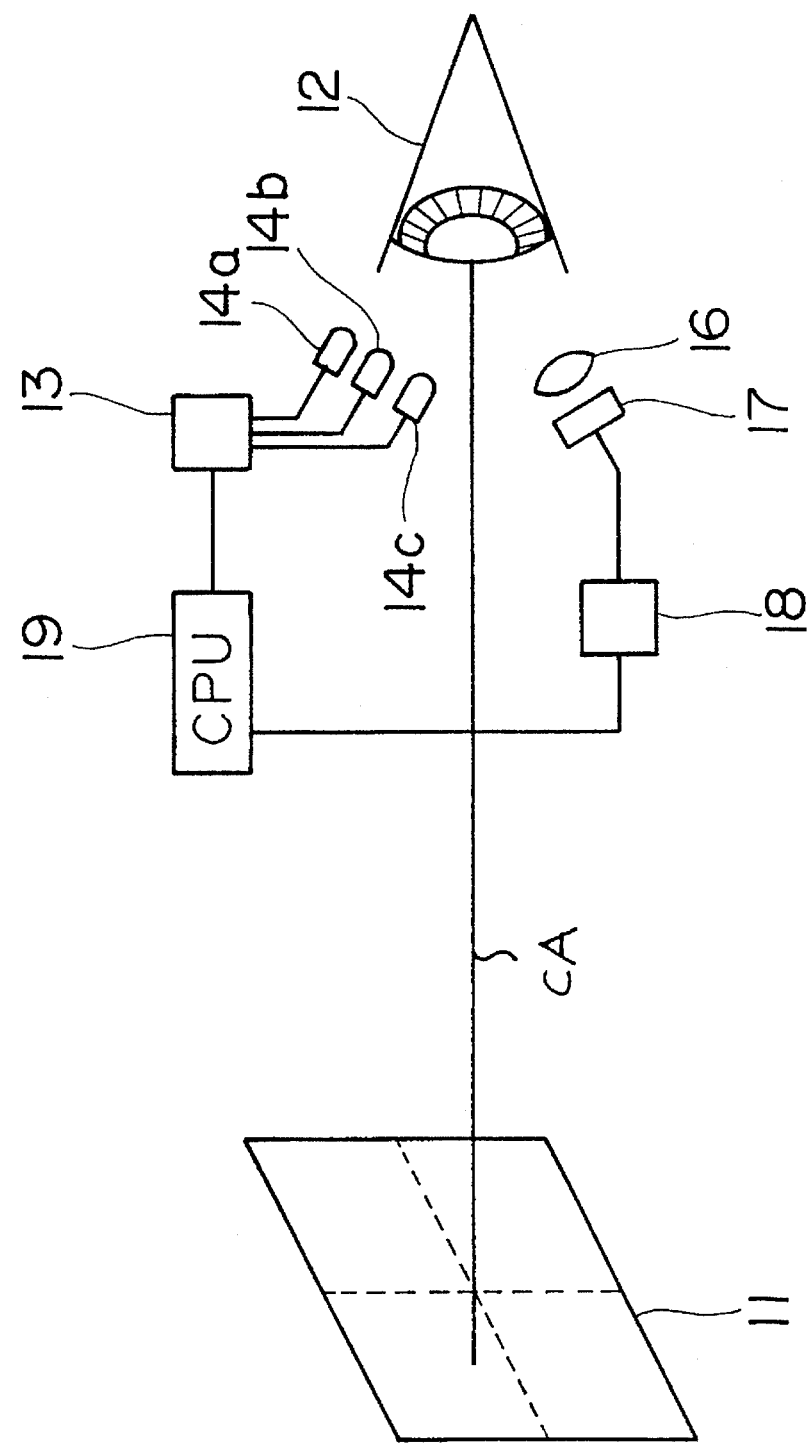
FIG. 10 is a figure showing another example of construction of a visual line detection device according to the second embodiment.

FIG. 10 is a constructional figure showing another example of disposition of the light sources 14 for visual line detection and of the photoelectric conversion device 17. In the example shown in FIG. 10, the converging lens 16 and the photoelectric conversion device 17 are disposed in positions which do not lie, in the optical sense, on the axis CA which passes through the central point of the field of observation 11.

Figure 11:
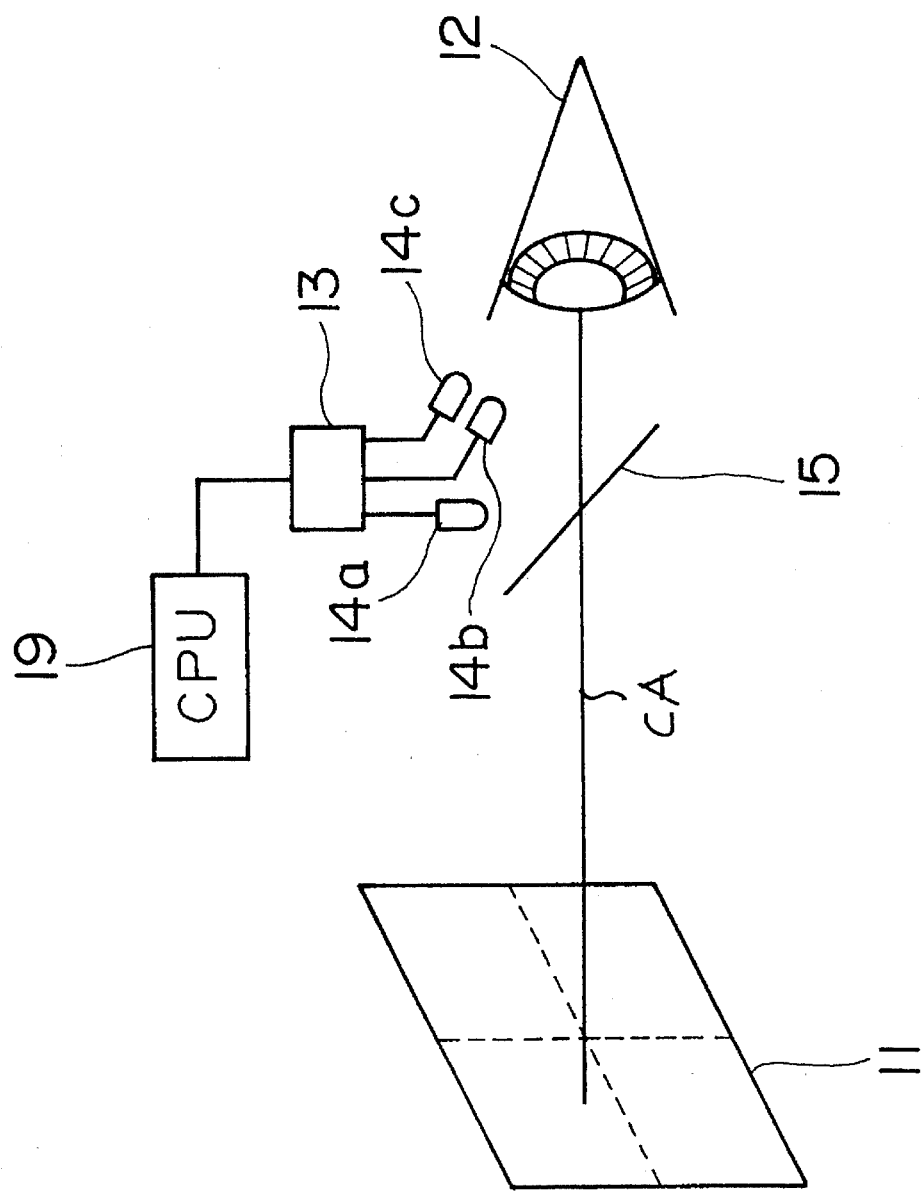
FIG. 11 is a figure showing yet another example of construction of a visual line detection device according to the second embodiment.
Figure 12:
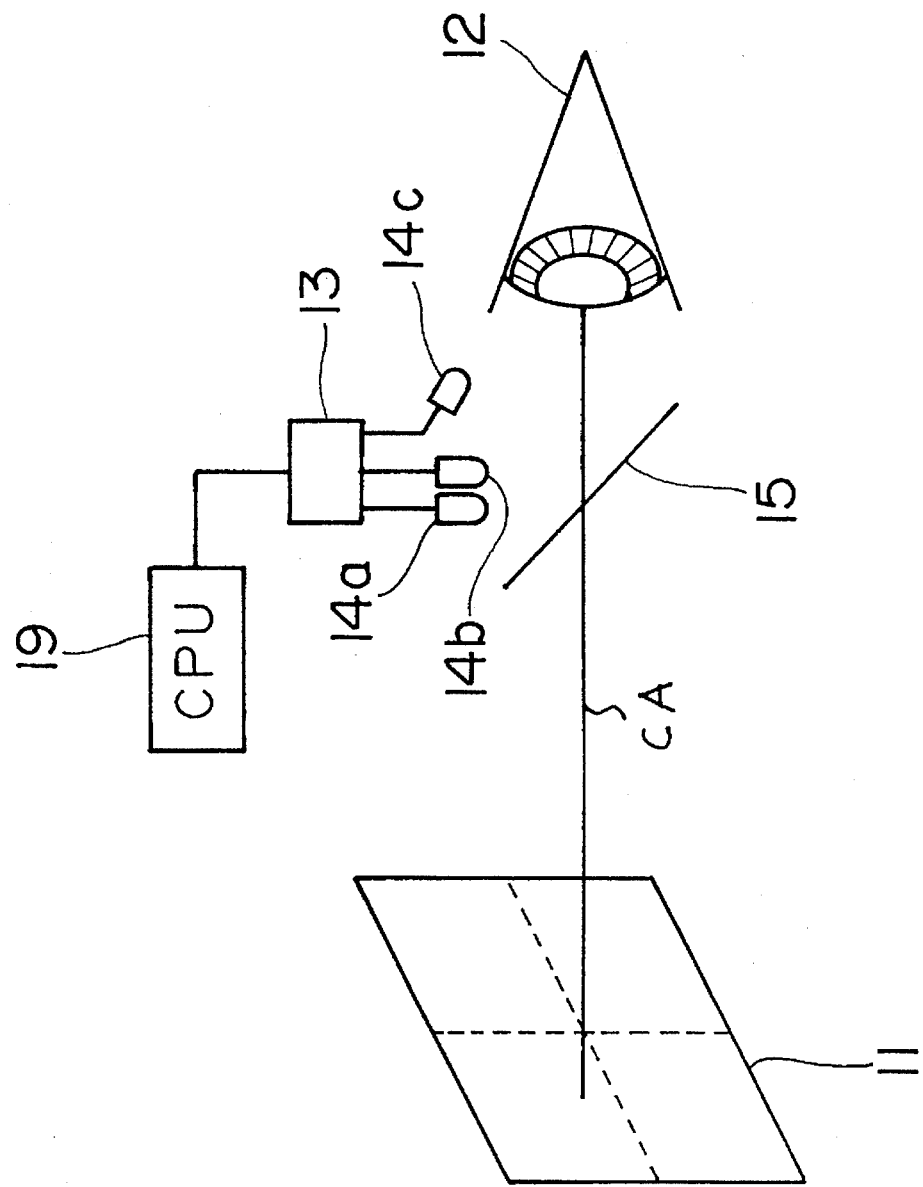
FIG. 12 is a figure showing still yet another example of construction of a visual line detection device according to the second embodiment.
Figure 13:
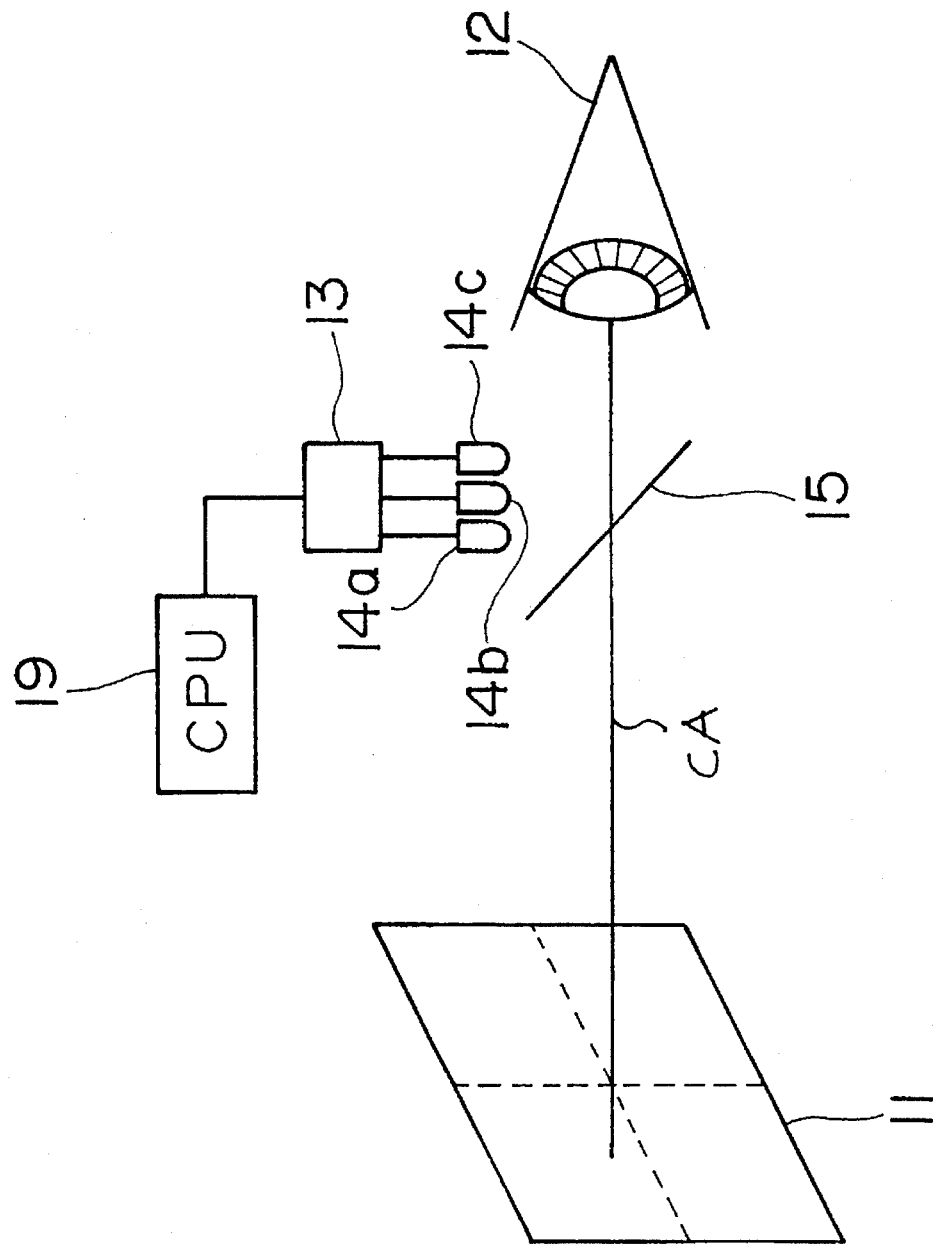
FIG. 13 is a figure showing still yet another example of construction of a visual line detection device according to the second embodiment.

FIGS. 11 through 13 are constructional figures showing yet other examples of disposition of the light sources 14 for visual line detection and of the photoelectric conversion device 17. In the examples shown in these figures, some of the light sources from the three light sources for visual line detection 14a through 14c are disposed in positions which do not obstruct via the dichroic mirror etc. the field of view within the field of observation 11 which this eyeball 12 of the observer is observing. In these figures, although the photoelectric conversion device 17 is deleted from the drawing for purposes of clarity, in fact the photoelectric conversion device 17 is disposed between the field of observation 11 and the eyeball 12 of the observer, either on the axis CA which passes through the central point of this field of observation 11, or at a position separated from this axis CA.

In FIG. 11, the one 14a of the light sources for visual line detection is disposed in the field of observation 11 via the dichroic mirror 15, while the others 14b and 14c of the light sources for visual line detection are disposed in close proximity to the eyeball 12 of the observer. In FIG. 12, the two ones 14a and 14b of the light sources for visual line detection are disposed in the field of observation 11 via the dichroic mirror 15, while the other one 14c of the light sources for visual line detection is disposed in close proximity to the eyeball 12 of the observer. And, in FIG. 14(A)–14(D), all 14a through 13c of the light sources for visual line detection are disposed in the field of observation 11 via the dichroic mirror 15. Illuminating the eyeball 12 of the observer via the dichroic mirror 15, etc. is advantageous in that the light rays emanating from the light source 14a, for example, can illuminate the eyeball 12 of the observer without obstruction of light rays by the eyelid, the eyelashes, or the like. Furthermore, as shown in FIGS. 11 and 12, disposing one of the light sources in the field of observation 11 via the dichroic mirror 15 increases the degree of freedom in construction.

FIGS. 14(A) through (D) are figures showing, when the eyeball 12 of the observer is positioned squarely against the center of the aforementioned field of observation 11, the state of disposition of the light sources 14 for visual line detection when this eyeball 12 of the observer is observing the field of observation 11. In these figures 14(A) through (D), three IREDs $14_1$ through $14_3$ are used for the light sources 14 for visual line detection.

Figure 14A:
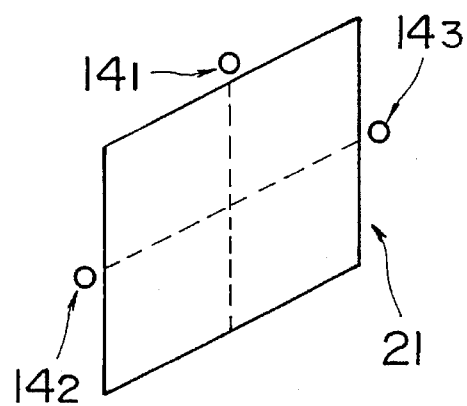
FIGS. 14(A) through 14(D) are figures showing examples of the disposition of the light sources for visual line detection according to the second embodiment.
Figure 14B:
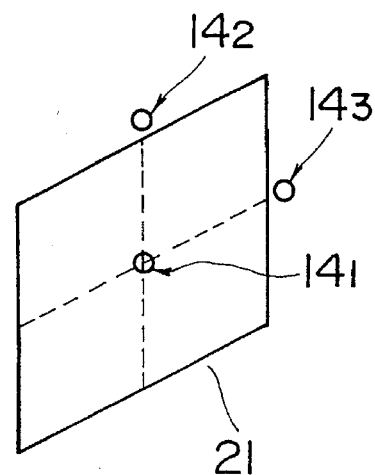
Figure 14C:
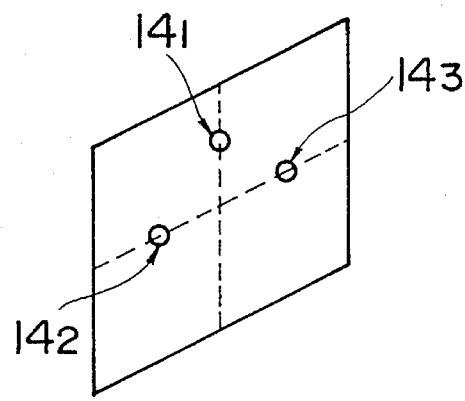
Figure 14D:
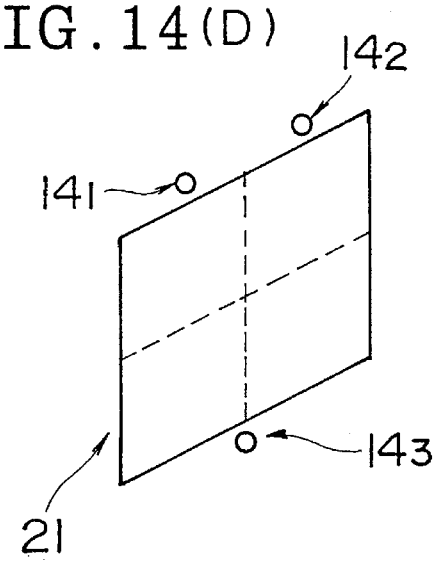

In FIG. 14(A), IRED$14_1$ is at the upper portion of the visual field frame 21, while IRED$14_2$ and IRED$14_3$ are disposed respectively at the left and the right of the visual field frame 21, so that the values (Sx, Sz) of the coordinates of IRED$14_1$ to IRED$14_3$ satisfy $Sx_1=0$, $Sx_2=-Sx_3$, and $Sz_2=-Sz_3$. FIG. 14(B) shows an example in which IRED$14_1$ is disposed in the center of the visual field frame 21 via the dichroic mirror etc. as shown in FIG. 11, while IRED$14_2$ and IRED$14_3$ are disposed respectively at the upper portion and the right portion of the visual field frame 21. FIG. 14(C) shows an example in which all of IRED$14_1$ through IRED$14_3$ are disposed near the center of the visual field frame 21 via the dichroic mirror etc. as shown in FIG. 13. FIG. 14(D) shows an example in which both IRED$14_1$ and IRED$14_2$ are disposed at the upper portion of the visual field frame 21, while IRED$14_3$ is disposed at the lower portion of the visual field frame 21, so that the values (Sx, Sz) of the coordinates of IRED$14_1$ to IRED$14_3$ satisfy $Sx_1=-Sx_2$, $Sx_3=0$, and $Sz_1=Sz_2=-Sz_3$. It should be understood that in the example shown in FIG. 14(D), although the straight line joining IRED$14_1$ and IRED$14_2$ lies outside the visual field frame 21, even in this case visual line detection is possible, according to the principles of the present invention. And, further, these figures should not be considered as being limiting as far as the disposition of IRED$14_1$ to IRED$14_3$ are concerned, since, for example, it will be acceptable for these three IREDs to be disposed in any positions around the eyeball of the observer, provided that, however, no one of the IREDs lies on the line joining the other two thereof.

FIGS. 15A, 15B and 16 are flow charts showing visual line detection calculation by the visual line detection device of this second embodiment. First, in the steps S201 through S207 of FIGS. 15A and 15B, the same procedures are performed as in the case of the steps S101 through S107 shown in FIGS. 8A and 8B for the previously described first embodiment; and accordingly description thereof will be omitted in the interests of brevity of disclosure. Next, in the step S208, a decision is made as to whether or not the denominator $(Sx_1-X1_{p1})\times(Sz_2-Z2_{p1})-(Sx_2-X2_{p1})\times(Sz_1-Z1_{p1})$ of the above described equation (13) is less than or equal to a very small value E which is considered to be effectively equal to zero. and if the decision is YES then it has been deemed that the center C of curvature of the cornea 6 of the eyeball 12 of the observer is positioned on the straight line joining IRED$14_1$ and IRED$14_2$, and the flow of control next proceeds to the step S209. while if the decision is NO then it has been deemed that the center C of curvature of the cornea 6 of the eyeball 12 of the observer is not positioned on the straight line joining IRED$14_1$ and IRED$14_2$, and the flow of control skips the steps S209, S210, and S211, to pass next to the step S212.

In the steps S209 and S210, since it has been deemed that the center C of curvature of the cornea 6 of the eyeball 12 of the observer is positioned on the straight line joining IRED$14_1$ and IRED$14_2$, the procedure which will be adopted is to substitute IRED$14_3$ for IRED$14_1$, and accordingly the same procedure as in the previously described steps S204 and S205 is performed for IRED$14_3$, which is the third light source for visual line detection, and the values $(X3_{p1}, Z3_{p1})$ of the actual space coordinates of the first Purkinje image P3 created by IRED$14_3$ are determined. And next, in the step S211, $X3_{p1}$ and $Z3_{p1}$ are respectively substituted for $X1_{p1}$ and $Z1_{p1}$; and the flow of control continues to the step S212.

In the step S212, the values $(X1_{p1}, Z1_{p1})$ and $(X2_{p1}, Z2_{p1})$ of the coordinates of the first Purkinje image P1 (which at this point will actually be the coordinates of the first Purkinje image P3, if an YES decision was reached in the step S208) and the first Purkinje image P2 and the values $(Sx_1, Sz_1)$ and $(Sx_2, Sz_2)$ of the coordinates of the light source S1 (which at this point will actually be the coordinates of the light source S3, if a YES decision was reached in the step S208) and the light source S2 are substituted into the equations (13) and (14), and the values (Cx, Cz) of the coordinates of the center of curvature C of the cornea 6 are obtained; and these values (Cx, Cz) of the coordinates of the center of curvature C of the cornea 6 and the values $(X1_{p1}, Z1_{p1})$ and $(X2_{p1}, Z2_{p1})$ of the coordinates of the first Purkinje images P1 and P2, as well as the values (Xd, Zd) of the coordinates of the center D of the pupil, are substituted into equations (17) through (20), so as to obtain the values θ, L, Φ, and k which determine the visual line of the eyeball 12 of the observer.

Thus, in summary, it is seen that according to the above procedure it is possible directly to determine the position of the center C of curvature of the cornea 6 and accurately to obtain the values θ, L, Φ, and k which determine the visual line of the eyeball 12 of the observer using the position of the center C of curvature of the cornea 6.

In this embodiment, when the center of curvature C of the cornea 6 is found to be positioned on the straight line joining JRED$14_1$ and IRED$14_2$, the process of visual line detection is performed using IRED$14_2$ and IRED$14_3$; but, as an alternative, it would also be acceptable to perform the process of visual line detection using IRED$14_1$ and IRED$14_3$. Further, it would also be acceptable to provide four IREDs, and, when the center of curvature C of the cornea was found to be positioned on the straight line joining the two of these IREDs which primarily were to be used for visual line detection, to perform the process of visual line detection using the other two IREDs.

Example of Application to a Camera

In the following, various combinations will be described in which preferred embodiments of the visual line detection device of the present invention have been fitted to a single lens reflex camera (which hereinafter will just be termed a camera); and these combinations will constitute various preferred embodiments of the camera equipped with a visual line detection device which is another aspect of the present invention.

Figure 17:
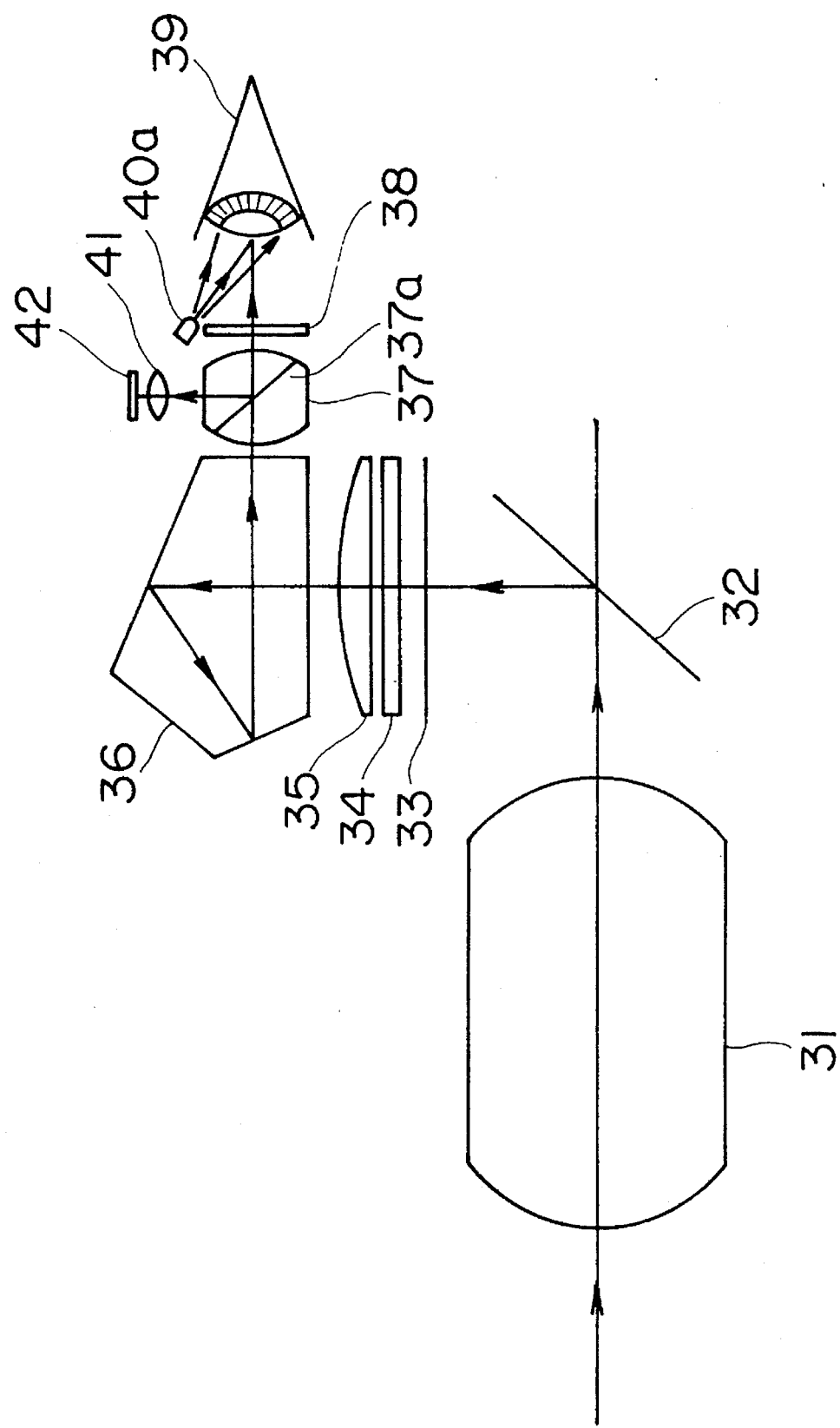
FIG. 17 is a simplified view of an optical system, showing an embodiment of the camera according to the present invention.

FIG. 17 is a simplified view showing an embodiment in which the visual line detection device shown in FIG. 1 has been fitted to a camera. Referring to this figure, 31 is a photographic lens which, although being shown as a single lens for the sake of convenience, may in practice be made up from a plurality of lenses, 32 is a reflex mirror, 33 is a display device, 34 is a focusing screen, 35 is a condenser lens, 36 is a pentagonal prism, and 37 is an eyepiece which, although being shown as a single lens for the sake of convenience, may in practice be made up from a plurality of lenses, and is provided with a dichroic mirror 37a which serves as a light ray dividing device. 38 is an eyepiece glass which has no optical power and which prevents dust or water droplets or the like from entering into the interior of the eyepiece, and 39 is the eyeball of an observer. 40a is a light source for visual line detection which is disposed in a position for directly illuminating the eyeball 39 of the observer from the periphery of the eyepiece glass 38. Moreover, in this embodiment, at least one other light source for visual line detection not shown in the figure is disposed in an identical manner in a position for directly illuminating the eyeball 39 of the observer from the periphery of the eyepiece glass 38. When a camera is equipped with a visual line detection device according to the present invention, it is desirable for light sources such as infrared light emitting diodes, which emit rays in the long wavelength region which cannot be seen by the eye, to be used as the light sources for visual line detection. 41 is a converging lens, and 42 is a photoelectric conversion device for which a light receptive two dimensional device such as a CCD sensor may be used.

Comparing this embodiment with the above described FIG. 4, the field of observation 11 of FIG. 5 corresponds to the visual field of the viewfinder of the camera, while the visual field frame 21 corresponds to the viewfinder eyepiece, when an observer is looking through the camera. Accordingly it is most desirable for the light sources for visual line detection to be disposed around the periphery of the viewfinder eyepiece. A concrete example is shown in FIGS. 18(A) and 18(B).

Figure 18A:
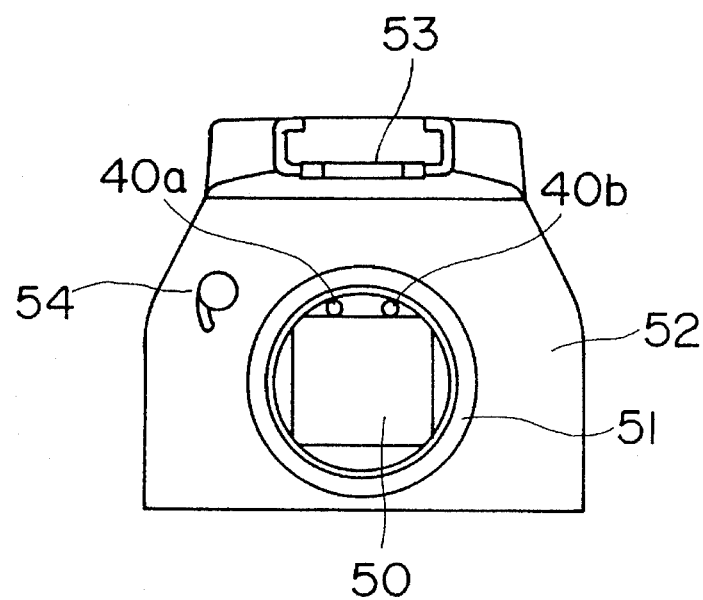
FIGS. 18(A) and 18(B) are elevation views showing a portion of the viewfinder of the FIG. 17 camera.
Figure 18B:
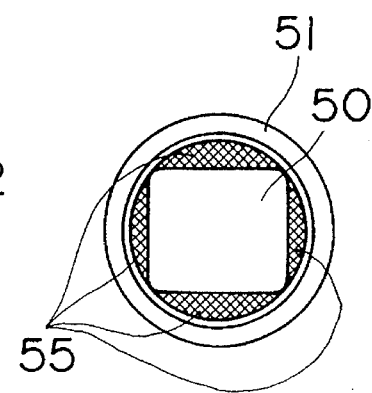

FIG. 18(A) and 18(B) is an elevation view showing a portion of the viewfinder of the camera shown in FIG. 17. Referring to FIG. 18(A), 40a and 40b are both light sources for visual line detection, 50 is a viewfinder eyepiece, 51 is an eyecap, 52 is the main body of the viewfinder, 53 is a clip-on type accessory shoe, and 54 is an eyepiece shutter lever. Further, although in FIG. 18(A) the light sources 40a and 40b for visual line detection are disposed on the upper edge of the viewfinder eyepiece 50, as an alternative, they could also be disposed in any positions on the hatched portions 55 shown in FIG. 18(B), i.e. in any positions below, above, to the left, or to the right of the viewfinder eyepiece 50. Further, it is also possible for three or more of the light sources 40 for visual line detection to be disposed on the periphery of the viewfinder eyepiece 50, and also in such a case they might as an alternative be disposed in any positions within the hatched portions 55 shown in FIG. 18(B), i.e. in any positions below, above, to the left, or to the right of the viewfinder eyepiece 50.

Figure 19:
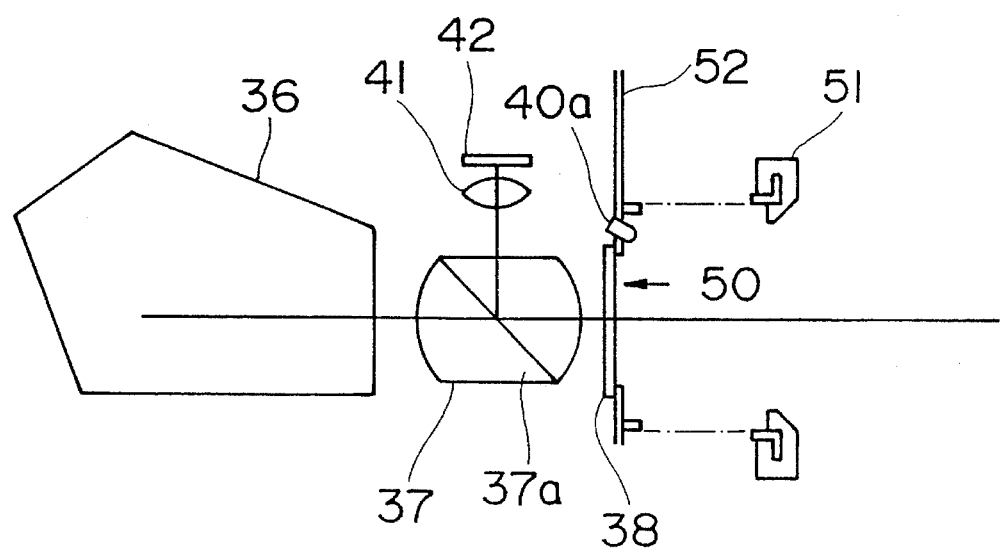
FIG. 19 is a sectional view showing a portion of the viewfinder of FIG. 17.

The positional relationship between the light source 40a for visual line detection, the eyepiece glass 38, and the eyecap 51 is as shown in FIG. 19. The eyepiece glass 38 is fixed in the viewfinder eyepiece 50 of the main body 52 of the viewfinder, and the eyecap 51 is provided with no optical system. In this way, the light source 40a for visual line detection directly illuminates the eyeball 12 of the observer, but does not illuminate the eyepiece glass 38.

The fact that the light source 40a for visual line detection directly illuminates the eyeball 12 of the observer has the following merits. That is, if said light source 40a for visual line detection were to illuminate the eyeball 12 of the observer via the dichroic mirror 37a like the photoelectric conversion device 42 of FIG. 19, then ghosts might occur due to reflection and the like inside the eyepiece 37, and there would be a danger that if these were focused on the photoelectric conversion device 42a negative influence might be exerted upon the visual line detection process. If on the other hand as shown in FIG. 17 the light source 40a for visual line detection directly illuminates the eyeball 12 of the observer, there can be no risk that ghosting can occur due to reflection and the like inside the eyepiece 37, and no negative influence can be exerted upon visual line detection. Further, the freedom of choice for the location of the light source 40a is enhanced, as compared to the case when the eyeball 12 of the observer is to be illuminated via the dichroic mirror 37a etc..

Figure 20:
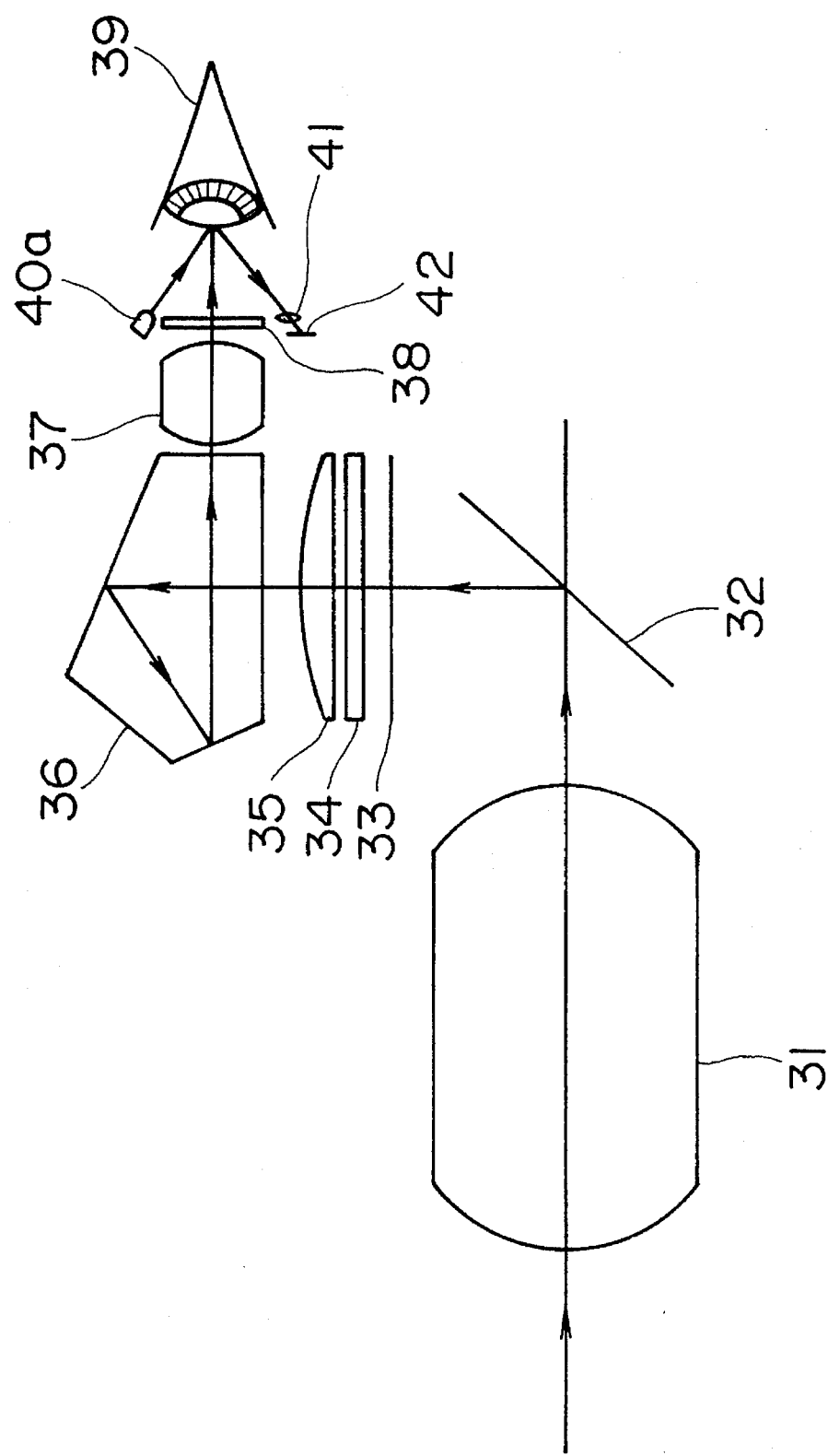
FIG. 20 is a simplified view of an optical system, showing another embodiment of the camera according to the present invention.
Figure 21A:
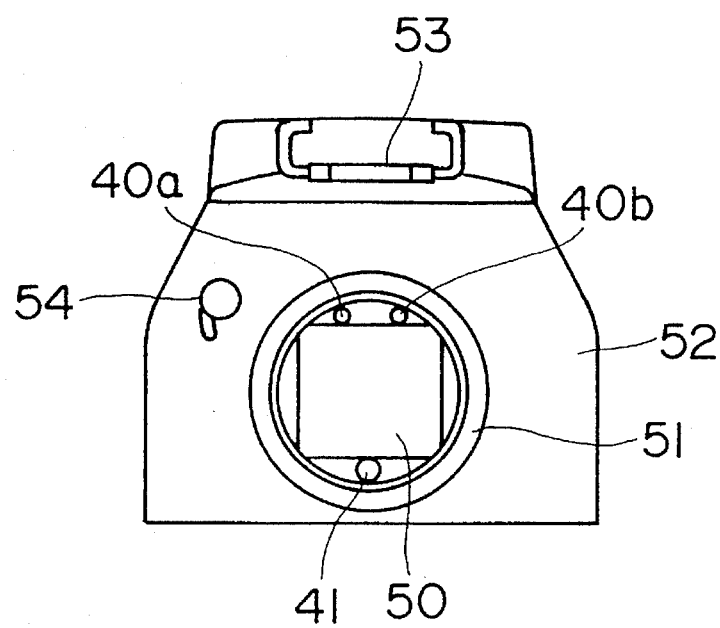
FIGS. 21(A) and 21(B) are elevation views showing a portion of the viewfinder of the FIG. 20 camera.
Figure 21B:
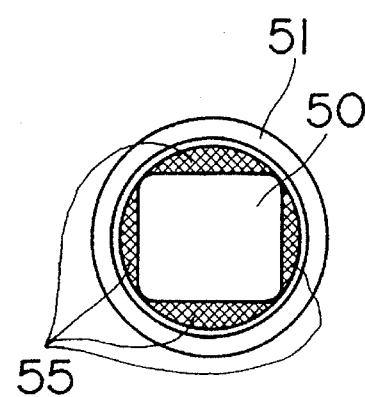
Figure 22:
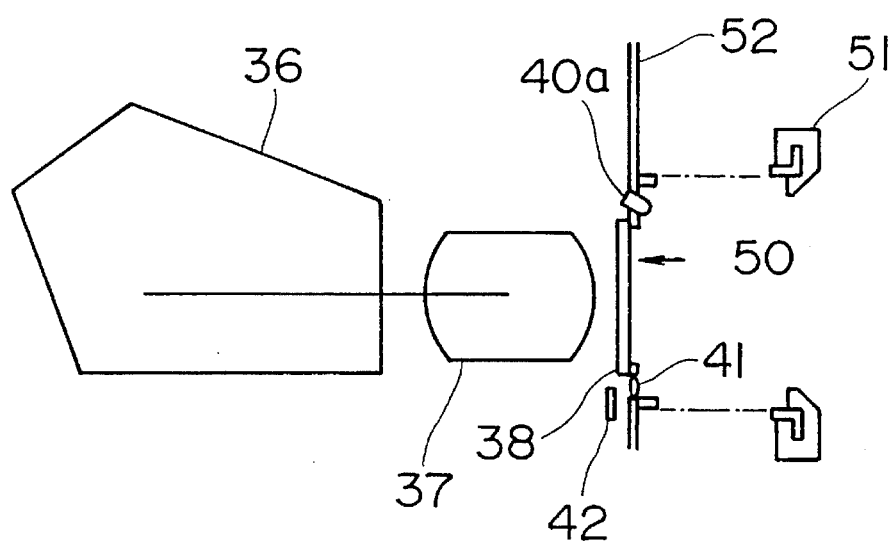
FIG. 22 is a sectional view showing a portion of the viewfinder of FIG. 21.

FIG. 20 is a simplified view showing an embodiment in which the visual line detection device shown in FIG. 2 has been fitted to a camera, and FIGS. 21(A) and 21(B) are elevation views showing a portion only of the viewfinder thereof. As shown in FIG. 20, a converging lens 41 and a photoelectric conversion device 42 are disposed in positions on the periphery of the eyepiece glass 38, just like the light sources 40a and 40b for visual line detection (shown in FIG. 20 only as the light source 40a). In this embodiment, it is not necessary for the eyepiece 37 to have any dichroic mirror such as the previous dichroic mirror 37a. As shown in FIG. 20 and FIG. 21(A), the light sources 40a and 40b for visual line detection are disposed along the upper edge of the viewfinder eyepiece 50, while the photoelectric conversion device 42 is disposed along the lower edge of the viewfinder eyepiece 50; but these light sources 40a, 40b and the photoelectric conversion device 42 could also be disposed in any positions on the hatched portions 55 shown in FIG. 21(B), i.e. in any positions below, above, to the left, or to the right of the viewfinder eyepiece 50. Further, it would also be possible for three or more such light sources for visual line detection to be disposed on the periphery of the viewfinder eyepiece 50, and in such a case they might alternatively be disposed in any positions within the hatched portions 55 shown in FIG. 21(B), i.e. in any positions below, above, to the left, or to the right of the viewfinder eyepiece 50. FIG. 22 is a view showing the positional relationships between the light source 40a for visual line detection and the converging lens 41, and the photoelectric conversion device 42, the eyepiece glass 38, and the eyecap 51.

Figure 23:
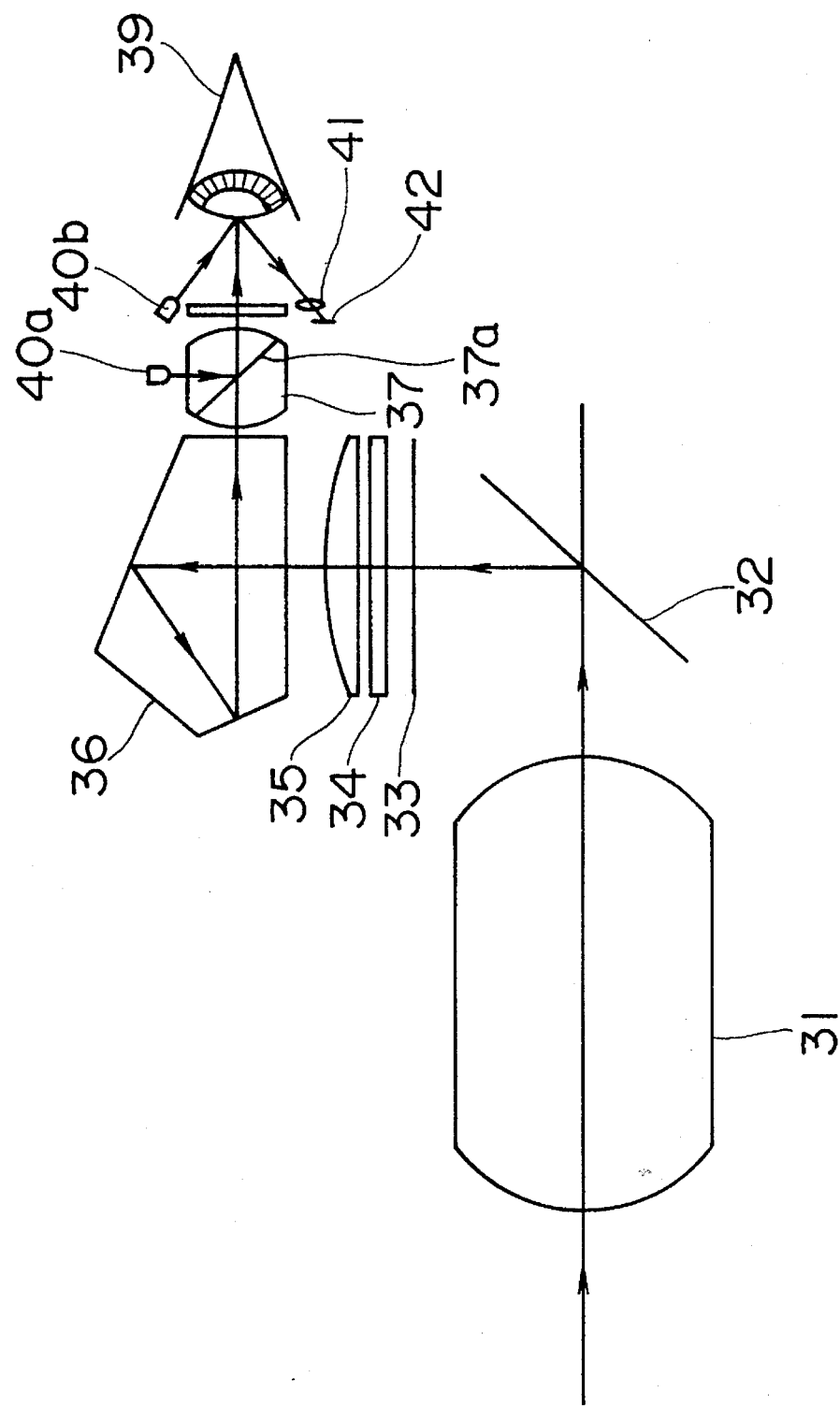
FIG. 23 is a simplified view of an optical system, showing yet another embodiment of the camera according to the present invention.
Figure 24:
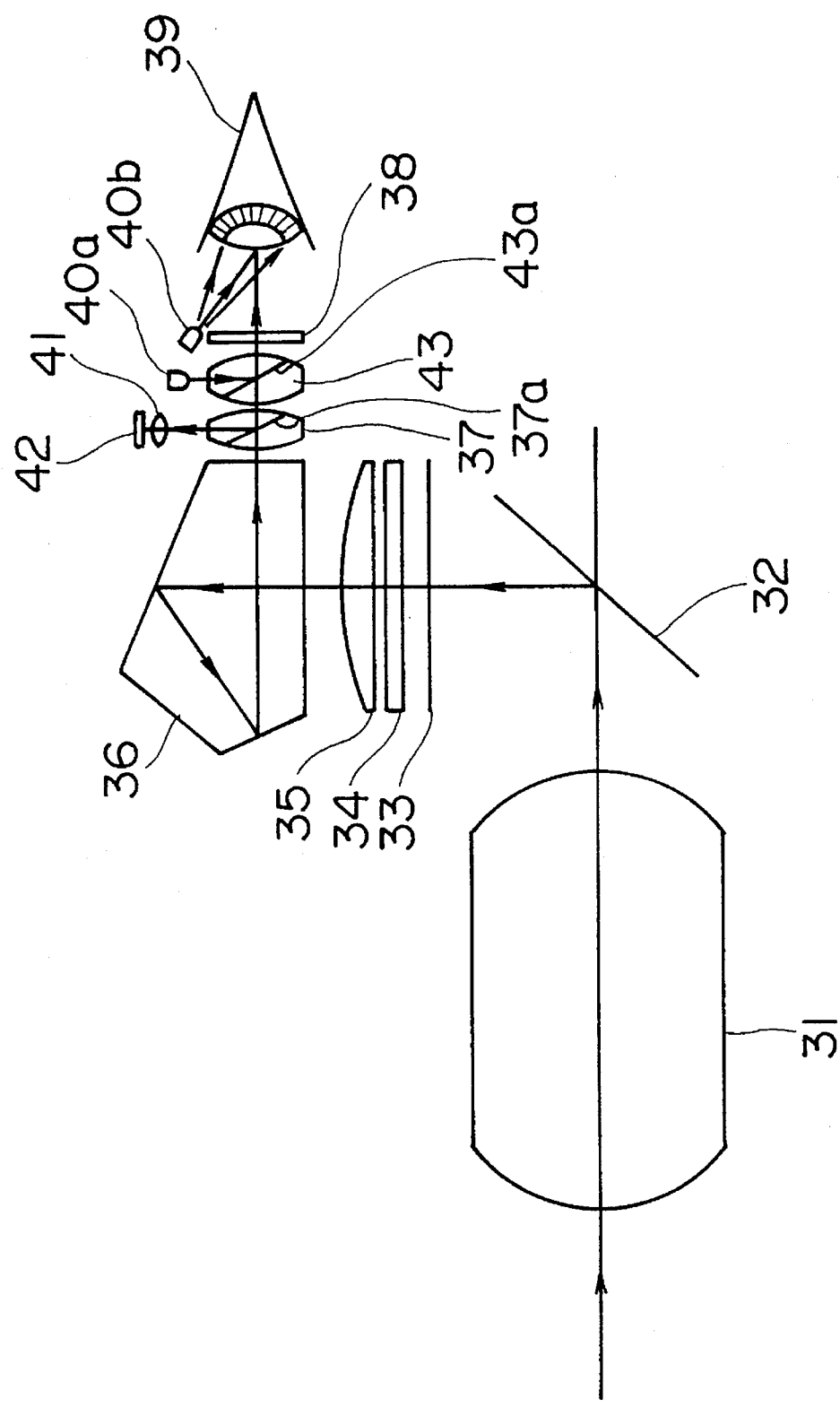
FIG. 24 is a simplified view of an optical system, showing still yet another embodiment of the camera according to the present invention.

FIG. 23 is a simplified view showing an embodiment in which the visual line detection device shown in FIG. 11 has been fitted to a camera. In the example shown in FIG. 23, only the one 40i aof the light sources is disposed within the viewfinder eyepiece 50 via the dichroic mirror 37a. When the light source 40a is disposed via the dichroic mirror 37a, the distances from the light sources 40a and 40b to the eyeball 12 of the observer differ comparatively greatly from one another, but this difference in distance does not exert any influence upon the performance of the visual line detection process. In FIG. 24, as a variation from the embodiment of FIG. 23, two dichroic mirrors 37a and 43a are used, and the light source 40b for visual line detection is disposed within the viewfinder eyepiece 50, while the light source 40a for visual line detection and the photoelectric conversion device 42 are disposed on the optical axis.

Figure 25:
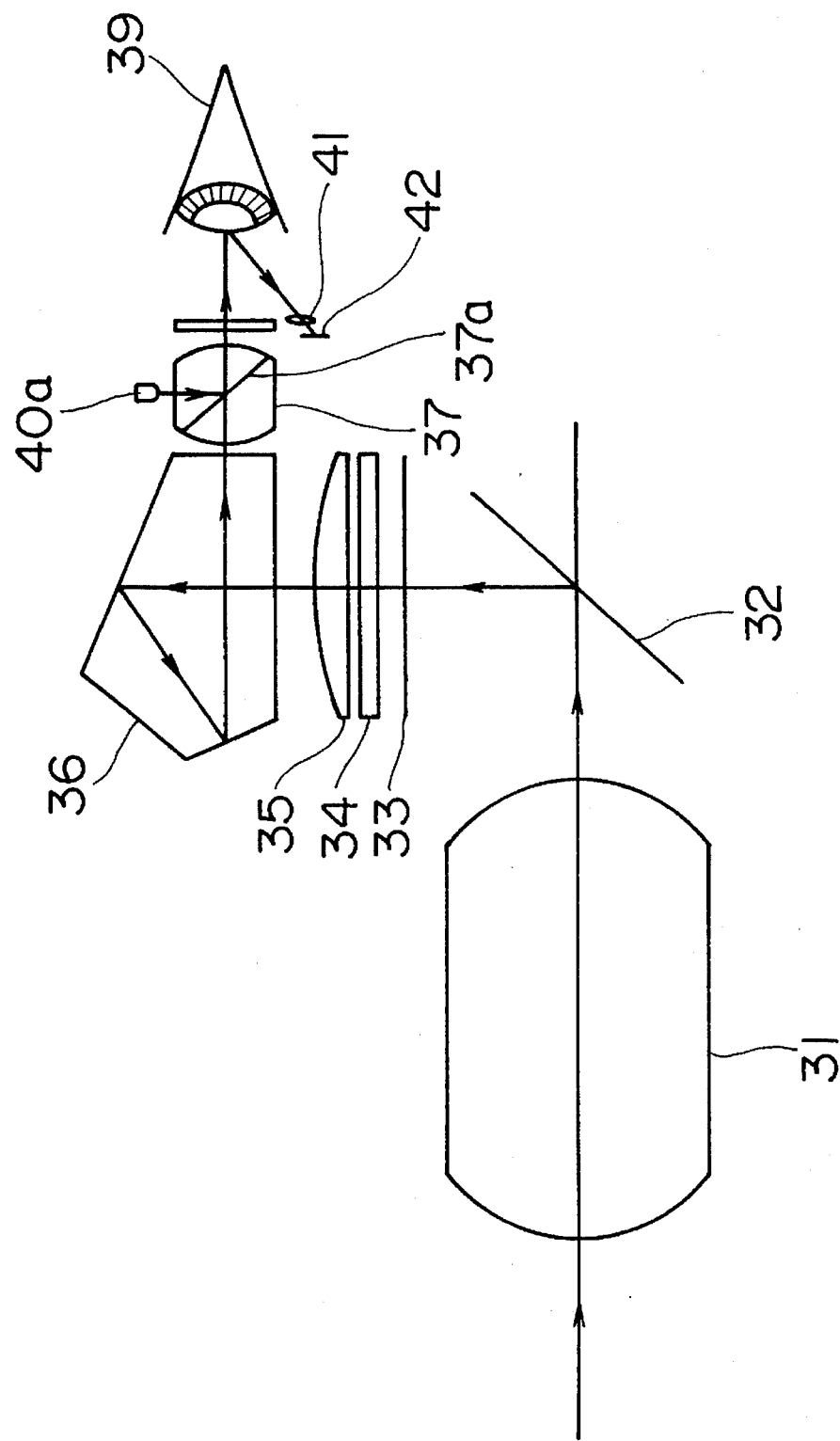
FIG. 25 is a simplified view of an optical system, showing still yet another embodiment of the camera according to the present invention.
Figure 26:
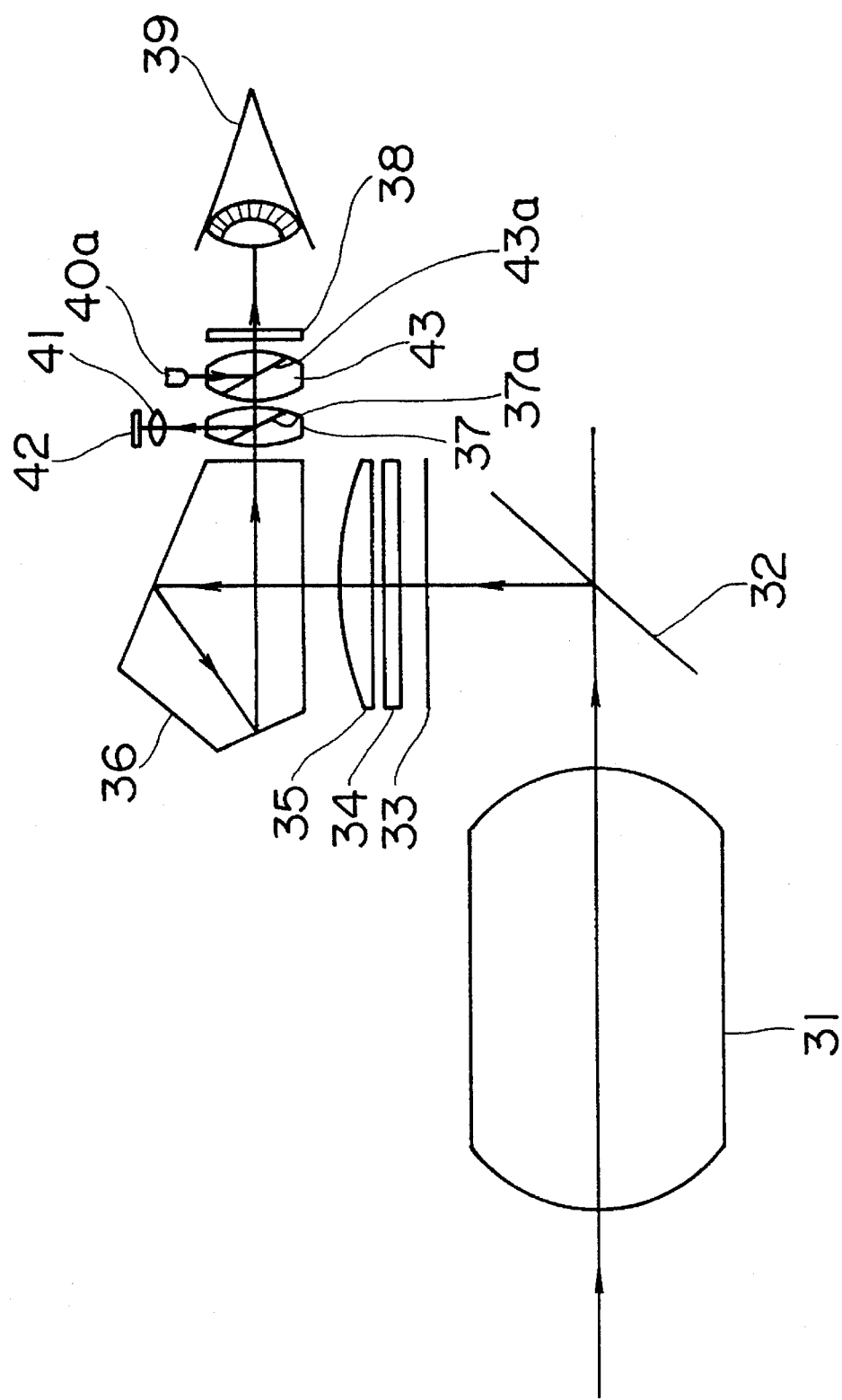
FIG. 26 is a simplified view of an optical system, showing still yet another embodiment of a camera according to the present invention.

FIG. 25 is a simplified view showing an embodiment in which the visual line detection device shown in FIG. 13 has been fitted to a camera. Although in this figure only one light source 40a is shown, actually all of the light sources 40 are disposed within the viewfinder eyepiece 50 via the dichroic mirror 37a. Further, the photoelectric conversion device 42 is disposed on the periphery of the viewfinder eyepiece 50. In FIG. 26, as a variation from the embodiment of FIG. 25, two dichroic mirrors 37a and 43a are used for disposing the light sources 40 for visual line detection (only one of which is shown in the drawing) within the viewfinder eyepiece 50 and for disposing the photoelectric conversion device 42 on the optical axis.

Figure 27:
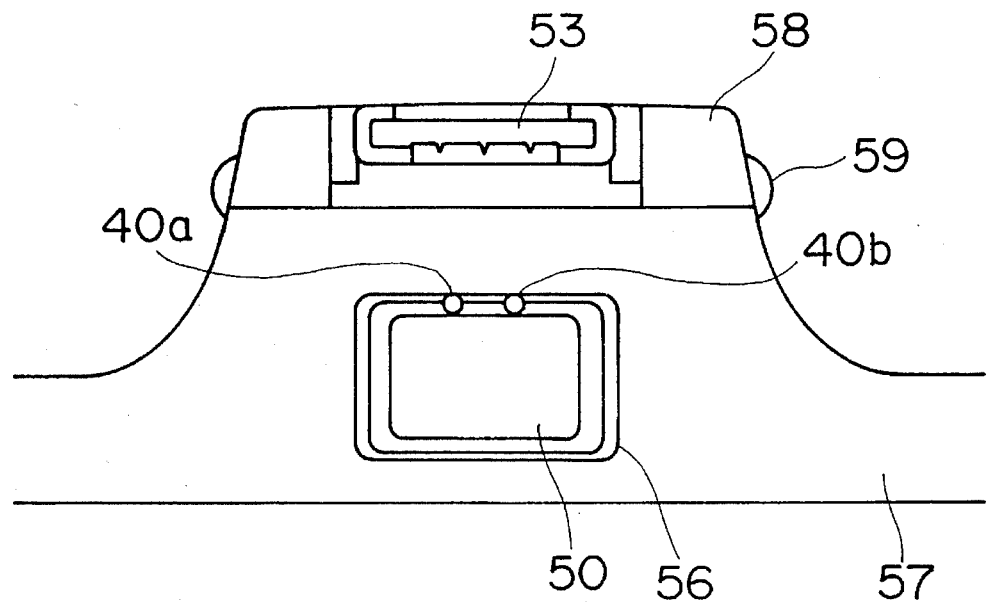
FIG. 27 is an elevation view showing the light sources for visual line detection of FIG. 1 arranged in a different layout and disposed in a portion of the viewfinder of a camera.

It should be understood that, with these examples of application of various preferred embodiments of the visual line detection device of the present invention to various cameras as described above, the fine details should not be considered as being limited to those described. FIG. 27 is an elevation view showing the case in which the visual line detection device shown in FIG. 1 is fitted to a different type of viewfinder. Referring to FIG. 27, 40a and 40b are both light sources for visual line detection, 50 is a viewfinder eyepiece, 53 is a clip-on type accessory shoe, and 56 is a member corresponding to the eyecap of FIG. 18, i.e. is a so called plane of view. 57 is the camera body, 58 is a pop up type flash device housed in the main body of the camera, and 59 is the pop up button for the flash device. In the camera shown in the drawing, since the construction is such that the plane of view 56 is directly fixed to the camera body 57, the light sources 40a and 40b for visual line detection can be directly disposed on the plane of view 56.

Figure 28:
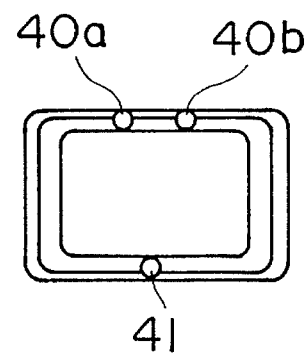
FIG. 28 is an elevation view showing the light sources for visual line detection of FIG. 2 and a photoelectric conversion device arranged in a different layout and disposed in a portion of the viewfinder of a camera.
Figure 29:
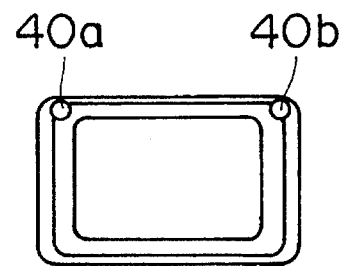
FIG. 29 is an example in which the light sources for visual line detection of FIG. 28 are disposed in the upper right of the portion of the viewfinder.

FIG. 28 is an elevation view showing the case in which the visual line detection device shown in FIG. 2 is fitted to a different type of viewfinder, and in this preferred embodiment a converging lens 41 and a photoelectric device 42 (not shown in the figure) are disposed on the plane of view 56. With such a viewfinder as described above, as shown in FIG. 29 it is also possible for the light sources 40a and 40b for visual line detection to be disposed at the corners of the viewfinder eyepiece 50, and accordingly the freedom for arrangement of the light sources is enhanced.

The present invention has been shown and described in terms of several preferred embodiments thereof, but is not to be considered as limited by any of the perhaps quite fortuitous details of said embodiments or of the drawings, but only by the terms of the appended claims, which follow.

I claim:

1. A visual line detection device which detects the visual line of an observer, comprising:

a light source which illuminates the eyeball of said observer; and a visual line direction calculating circuit which calculates the direction of the visual line of said observer using information related to said light source as one parameter.

2. A visual line detection device according to claim 1, wherein said information related to said light source is positional information related to a position of said light source.

3. A visual line detection device according to claim 2, further comprising a light receiving element which receives light which is reflected from the eyeball of said observer, and wherein:

said visual line direction calculating circuit calculates the direction of the visual line of said observer using the output from said light receiving element and said positional information related to said position of said light source.

4. A visual line detection device according to claim 3, wherein said visual line direction calculating circuit comprises a pupil center calculating section which calculates the pupil center from the output from said light receiving element, and a cornea center of curvature calculating section which calculates the cornea center of curvature from the output from said light receiving element and from said information related to said light source.

5. A visual line detection device according to claim 1, wherein said light source comprises a plurality of light source elements, at least one of which illuminates said eyeball directly and not via any optical system.

6. A visual line detection device according to claim 1, wherein said light source comprises a plurality of light source elements, at least one of which illuminates said eyeball via an optical system.

7. A visual line detection device according to claim 3, wherein said light source comprises at least three light source elements, and said visual line direction calculating circuit selects two reflected images from among the corneal reflected images formed by said light sources and output from said light receiving element, and detects the visual line based upon these selected corneal reflected images.

8. A visual line detection device according to claim 7, wherein said three light source elements are disposed so as to be non-collinear.

9. A visual line detection device according to claim 3, wherein said light receiving element receives a reflected image from the eyeball of said observer not via any optical system.

10. A camera comprising:

a viewfinder device which comprises a viewfinder eyeball contact window and a viewfinder optical system;

a visual line detection device which detects the direction of the visual line of an observer looking through said viewfinder eyeball contact window from a reflected image from the eyeball of said observer;

a light source which illuminates the eyeball of said observer; and a visual line direction calculating circuit which calculates the direction of the visual line of said observer using information related to said light source as one parameter.

11. A camera according to claim 10, wherein said information related to said light source is positional information related to a position of said light source.

12. A camera according to claim 11, further comprising a light receiving element which receives light which is reflected from the eyeball of said observer, and wherein:

said visual line direction calculating circuit calculates the direction of the visual line of said observer using the output from said light receiving element and said positional information related to said position of said light source.

13. A camera according to claim 12, wherein said visual line direction calculating circuit comprises a pupil center calculating section which calculates the pupil center from the output from said light receiving element, and a cornea center of curvature calculating section which calculates the cornea center of curvature from the output from said light receiving element and from said information related to said light source.

14. A camera according to claim 10, wherein said light source comprises a plurality of light source elements, at least one of which is disposed at a periphery of said viewfinder eyeball contact window and illuminates said eyeball directly and not via said viewfinder optical system.

15. A camera according to claim 10, wherein said light source comprises a plurality of light source elements, at least one of which illuminates said eyeball via said viewfinder optical system.

16. A camera according to claim 12, wherein said light source comprises at least three light source elements, and said visual line direction calculating circuit selects two reflected images from among the corneal reflected images formed by said light sources and output from said light receiving element, and detects the visual line based upon these selected corneal reflected images.

17. A camera according to claim 12, wherein said light receiving element is disposed at a periphery of said viewfinder eyeball contact window and receives a reflected image from the eyeball of said observer not via any optical system.

* * * * *